United States Patent
Pomper et al.

(10) Patent No.: US 10,717,750 B2
(45) Date of Patent: *Jul. 21, 2020

(54) 68GA-LABELED NOTA-CHELATED PSMA-TARGETED IMAGING AND THERAPEUTIC AGENTS

(71) Applicant: THE JOHNS HOPKINS UNIVERSITY, Baltimore, MD (US)

(72) Inventors: Martin G. Pomper, Baltimore, MD (US); Ronnie C. Mease, Fairfax, VA (US); Sangeeta Ray, Ellicott City, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/557,854

(22) PCT Filed: Mar. 14, 2016

(86) PCT No.: PCT/US2016/022309
§ 371 (c)(1),
(2) Date: Sep. 13, 2017

(87) PCT Pub. No.: WO2016/149188
PCT Pub. Date: Sep. 22, 2016

(65) Prior Publication Data
US 2018/0051039 A1 Feb. 22, 2018
US 2019/0023722 A9 Jan. 24, 2019

Related U.S. Application Data

(60) Continuation of application No. 14/243,535, filed on Apr. 2, 2014, now Pat. No. 9,776,977, which is a division of application No. 13/257,499, filed as application No. PCT/US2010/028020 on Mar. 19, 2010, now Pat. No. 9,056,841.

(60) Provisional application No. 62/132,955, filed on Mar. 13, 2015, provisional application No. 61/248,934, filed on Oct. 6, 2009, provisional application No. 61/248,067, filed on Oct. 2, 2009, provisional application No. 61/161,484, filed on Mar. 19, 2009, provisional application No. 61/161,485, filed on Mar. 19, 2009.

(51) Int. Cl.
*C07F 5/00* (2006.01)
*A61K 51/04* (2006.01)

(52) U.S. Cl.
CPC .......... *C07F 5/003* (2013.01); *A61K 51/0497* (2013.01)

(58) Field of Classification Search
CPC ............................ C07F 5/003; A61K 51/0497
See application file for complete search history.

(56) References Cited

U.S. PATENT DOCUMENTS

| | | | |
|---|---|---|---|
| 9,694,091 B2* | 7/2017 | Pomper | A61K 31/145 |
| 10,039,845 B2* | 8/2018 | Pomper | A61K 31/145 |
| 2014/0241985 A1* | 8/2014 | Berkman | A61K 51/0497 |
| | | | 424/1.77 |

OTHER PUBLICATIONS

Banerjee et al., J. Med. Chem., 2014, 57, p. 2657-2669.*

* cited by examiner

*Primary Examiner* — Michael G. Hartley
*Assistant Examiner* — Leah H Schlientz
(74) *Attorney, Agent, or Firm* — Casimir Jones, S.C.; Jeffrey W. Childers

(57) ABSTRACT

PSMA-targeted PET/SPECT agents for imaging PSMA-positive cancer and or tumor neovasculature and PSMA-targeted radiotherapeutic agent for the treatment of PSMA-positive cancer or tumor neovasculature are disclosed. Methods of imaging PSMA expressing tumors, or cells and kits also are disclosed.

12 Claims, 9 Drawing Sheets

68GA-LABELED NOTA-CHELATED PSMA-TARGETED IMAGING AND THERAPEUTIC AGENTS

CROSS-REFERENCE TO RELATED APPLICATIONS

This application is a 35 U.S.C. § 371 National Stage Entry of International Application No. PCT/US16/022309 having an international filing date of Mar. 14, 2016, which claims the benefit of U.S. Provisional Application No. 62/132,955, filed Mar. 13, 2015, the contents of which are incorporated herein by reference in their entirety.

This application also is a continuation-in-part of and claims priority to U.S. patent application Ser. No. 14/243,535, filed Apr. 2, 2014, now U.S. Pat. No. 9,776,977, which is a divisional of U.S. patent application Ser. No. 13/257,499, filed Sep. 19, 2011, now U.S. Pat. No. 9,056,841, which is a 35 U.S.C. § 371 National Stage Entry of International Application No. PCT/US2010/028020, having an international filing date of Mar. 19, 2010, which claims the benefit of U.S. Provisional Application nos. 61/161,485, filed Mar. 19, 2009, 61/161,484, filed Mar. 19, 2009, 61/248,067, filed Oct. 2, 2009, and 61/248,934, filed Oct. 6, 2009.

FEDERALLY SPONSORED RESEARCH OR DEVELOPMENT

This invention was made with government support under CA148901, CA151838, CA134675, CA184228, CA183031, and CA092871 awarded by the National Institutes of Health. The government has certain rights in the invention.

BACKGROUND

According to the National Cancer Institute approximately 220,800 cases of prostate cancer will be diagnosed in 2015, with over 27,540 cases proving to be lethal (about 12.5%) (Institute, N. C. Cancer Statistics (2015)). Existing imaging techniques for detection and therapeutic monitoring of prostate cancer are inadequate for effective management of the disease. The transmembrane glycoprotein prostate-specific membrane antigen (PSMA) is increasingly recognized as an important target for both imaging and therapy of prostate cancer (Afshar-Oromieh et al. (2014) *Eur J Nucl Med Mol Imaging*; Afshar-Oromieh et al., (2013) *Eur J Nucl Med Mol Imaging* 40, 486-95). PSMA is found in benign, as well as in malignant prostate tissue (Murphy et al., (1995) *Prostate* 26, 164-8; Murphy et al., (1998) *Urology* 51, 89-97; Murphy et al., (1998) *J Urol* 160, 2396-401). However, expression of PSMA is greatest in prostate adenocarcinoma, particularly in castration-resistant disease (Sweat et al. (1998) *Urology* 52, 637-40; Silver et al. (1997) *Clin Cancer Res* 3, 81-5). PSMA is also present in the neovasculature of solid tumors including kidney, lung (Wang et al. (2015) *PLoS ONE* 10.), stomach, colon, and breast (Haffner et al. (2009) *Hum Pathol* 40, 1754-61; Haffner et al (2012) *Mod Pathol* 25, 1079-85; Baccala et al. (2007) *Urology* 70, 385-90). Expression of PSMA is associated with the neovascular endothelium in non-prostate tumors (Chang et al. (1999) *Mol Urol* 3, 313-320; Chang et al. (1999) *Clin Cancer Res* 5, 2674-81).

PSMA-targeted agents to image patients with prostate cancer using positron emission tomography (PET) have been reported by several groups (Cho et al. (2012) *J Nucl Med* 53, 1883-91; Afshar-Oromieh et al. (2012) *Eur J Nucl Med Mol Imaging* 39, 1085-6; Afshar-Oromieh et al. (2013) *Eur J Nucl Med Mol Imaging* 40, 1629-30; Afshar-Oromieh et al. (2014) *Eur J Nucl Med Mol Imaging* 41, 887-97; Afshar-Oromieh et al. (2015) *Eur. J. Nuc.l Med. Mol. Imaging* 42, 197-209; Eiber et al. (2015) *J Nucl Med* 56, 668-74; Eiber et al. (2014) *Abdom Imaging*; Rowe et al. (2015) *J Nucl Med* 56, 1003-10). Although there are debatable advantages and disadvantages with respect to which isotope to use for detection with PET, namely $^{18}$F vs. $^{68}$Ga, the radiometal $^{68}$Ga can be produced on-site with a generator, followed by simple synthesis of the radiotracer (Fani et al. (2008) *Contrast media & molecular imaging* 3, 67-77). $^{68}$Ga-1, a radiotracer that employed the DOTA-mono-amide chelator with conjugation to $H_2N$-Lys-$(CH_2)_3$-Lys-urea-Glu for targeting to PSMA (FIG. 1) has been previously reported (Banerjee et al. (2010) *J Med Chem* 53, 5333-41). That chelator has been chosen to make it possible to complex imaging radiometals, such as $^{68}$Ga, $^{86}$Y, $^{203}$Pb, as well as therapeutic radiometal nuclides, such as $^{177}$Lu, $^{90}$Y, $^{212}$Pb or $^{225}$Ac, within the same scaffold.

Two $^{68}$Ga-based agents have demonstrated excellent clinical results for detection of prostate cancer, namely, $^{68}$Ga-DKFZ-PSMA-11 (Glu-urea-Lys-(Ahx)-HBED-CC) and EuK-Sub-kff-$^{68}$Ga-DOTAGA ($^{68}$Ga-PSMA I&T) (Herrmann et al. (2015) *Journal of Nuclear Medicine*; Eder et al. (2012) *Bioconjug Chem* 23, 688-97; Weineisen et al. (2015) *J Nucl Med*; Weineisen et al. (2014) *EJNMMI Res* 4, 63). Those compounds both employ the Glu-Lys-urea-based PSMA-targeted moiety, while $^{68}$Ga-DOTA-DUPA-Pep, also recently tested clinically, uses DOTA-monoamide as the chelating agent and Glu-Glu-urea as the PSMA-targeting moiety (Reske et al. (2013) *Mol Imaging* 40, 969-70). A recent preclinical study also evaluated $^{68}$Ga-(CHX-A"-DTPA)-Pep using CHX-A"-DTPA as the chelating agent (Baur et al. (2014) *Pharmaceuticals (Basel)* 7, 517-29). Among the agents, $^{68}$Ga-DKFZ-PSMA-11 has been most widely studied clinically (Afshar-Oromieh et al. (2013) *Eur J Nucl Med Mol Imaging* 40, 486-95; Afshar-Oromieh et al. (2012) *Eur J Nucl Med Mol Imaging* 39, 1085-6; Afshar-Oromieh et al. (2013) *Eur J Nucl Med Mol Imaging* 40, 1629-30; Afshar-Oromieh et al. (2014) *Eur J Nucl Med Mol Imaging* 41, 887-97; Afshar-Oromieh et al. (2015) *Eur. J. Nuc.l Med. Mol. Imaging* 42, 197-209; Afshar-Oromieh et al. (2013) *Eur J Nucl Med Mol Imaging* 40, 971-2; Mottaghy et al. (2015) *European Journal of Nuclear Medicine and Molecular Imaging* 1-3. The growing number of clinical trials employing $^{68}$Ga-based, PSMA-targeted PET provides rationale to investigate structural elements that could promote the least off-target uptake of this class of radiotracers.

SUMMARY

In some aspects, the presently disclosed subject matter provides a compound of Formula (I):

(I)

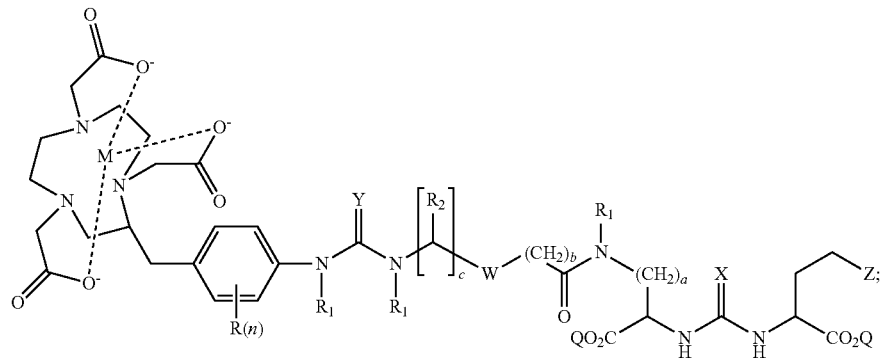

wherein: Z is tetrazole or $CO_2Q$; Q is H or a protecting group; X and Y are each independently O or S; a is an integer selected from the group consisting of 1, 2, 3 and 4; b and c are each independently an integer selected from the group consisting of 0, 1, 2, 3, 4, 5, 6, 7, 8, 9, and 10; W is selected from the group consisting of —C(=O)—$NR_4$—, —$NR_4$—C(=O)—, —$NR_4$C(=O)—$NR_4$—, —$NR_4$—C(=S)—$NR_4$—, —$NR_4$—C(=O)—O—, —O—C(=O)—$NR_4$—, —O—C(=O)—, and —C(=O)—O—; each $R_1$ is independently H or $C_1$-$C_4$ alkyl; each $R_2$ is independently H or —$COOR_3$, wherein each $R_3$ is independently H or a $C_1$-$C_6$ alkyl; each $R_4$ is independently H or $C_1$-$C_4$ alkyl; each R is independently selected from the group consisting of hydrogen, halogen, alkyl, alkenyl, alkynyl, aryl, heteroaryl, alkyaryl, arylakyl, and alkylheteroaryl; n is an integer selected from the group consisting of 0, 1, 2, 3 and 4; and M is a metal; and pharmaceutically acceptable salts thereof.

In particular aspects of the compound of the Formula (I), the metal (M) is selected from the group consisting of Tc-94m, Tc-99m, In-111, Ga-67, Ga-68, Y-86, Y-90, Lu-177, Re-186, Re-188, Cu-64, Cu-67, Co-55, Co-57, Sc-47, Ac-225, Bi-213, Bi-212, Pb-212, Sm-153, Ho-166, Gd-152, or Dy-166.

In yet more particular aspects, the metal (M) is Ga-68.

In still more particular aspects, the compound of Formula (I) is $^{68}$Ga-SRV168.

In other aspects, the presently disclosed subject matter provides a method for imaging one or more prostate-specific membrane antigen (PSMA) tumors or cells, the method comprising contacting the one or more tumor or cells, with an effective amount of a compound of Formula (I) and making an image, the compound of Formula (I) comprising:

(I)

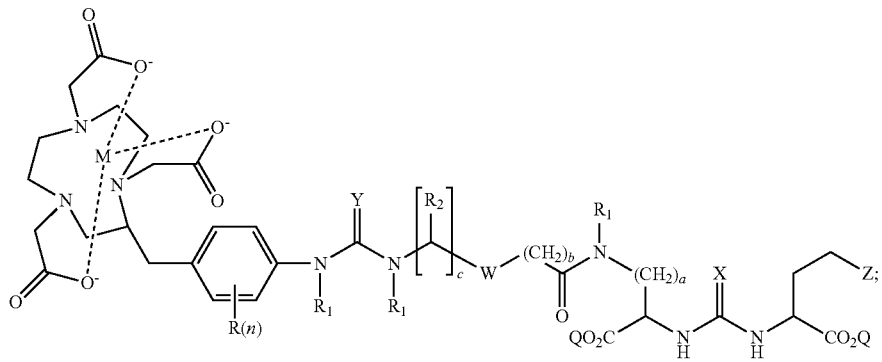

wherein: Z is tetrazole or $CO_2Q$; Q is H or a protecting group; X and Y are each independently O or S; a is an integer selected from the group consisting of 1, 2, 3 and 4; b and c are each independently an integer selected from the group consisting of 0, 1, 2, 3, 4, 5, 6, 7, 8, 9, and 10; W is selected from the group consisting of —C(=O)—$NR_4$—, —$NR_4$—C(=O)—, —$NR_4$C(=O)—$NR_4$—, —$NR_4$—C(=S)—$NR_4$—, —$NR_4$—C(=O)—O—, —O—C(=O)—$NR_4$—, —O—C(=O)—, and —C(=O)—O—; each $R_1$ is independently H or $C_1$-$C_4$ alkyl; each $R_2$ is independently H or —$COOR_3$, wherein each $R_3$ is independently H or a $C_1$-$C_6$ alkyl; each $R_4$ is independently H or $C_1$-$C_4$ alkyl; each R is independently selected from the group consisting of hydrogen, halogen, alkyl, alkenyl, alkynyl, aryl, heteroaryl, alkyaryl, arylakyl, and alkylheteroaryl; n is an integer selected from the group consisting of 0, 1, 2, 3 and 4; and M is a radioactive metal suitable for radiotherapy; and pharmaceutically acceptable salts thereof.

In some other aspects, the presently disclosed subject matter provides a method for treating or preventing a disease or condition associated with one or more PSMA expressing tumors or cells, the method comprising administering to a subject in need of treatment thereof, at least one compound of Formula (I), in an amount effective to treat or prevent the disease or condition. In yet other aspects, the presently disclosed subject matter provides a kit comprising a compound of Formula (I).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
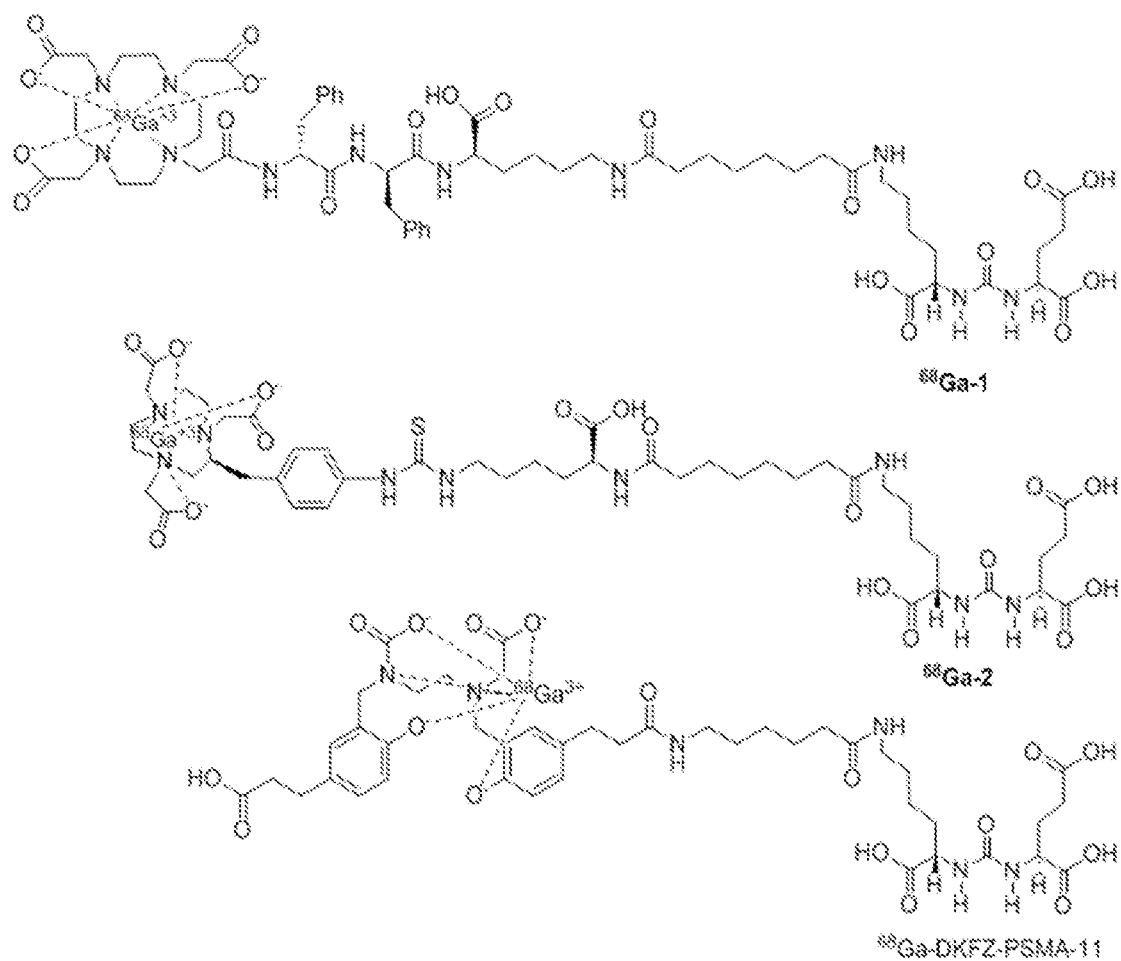
Figure 4:
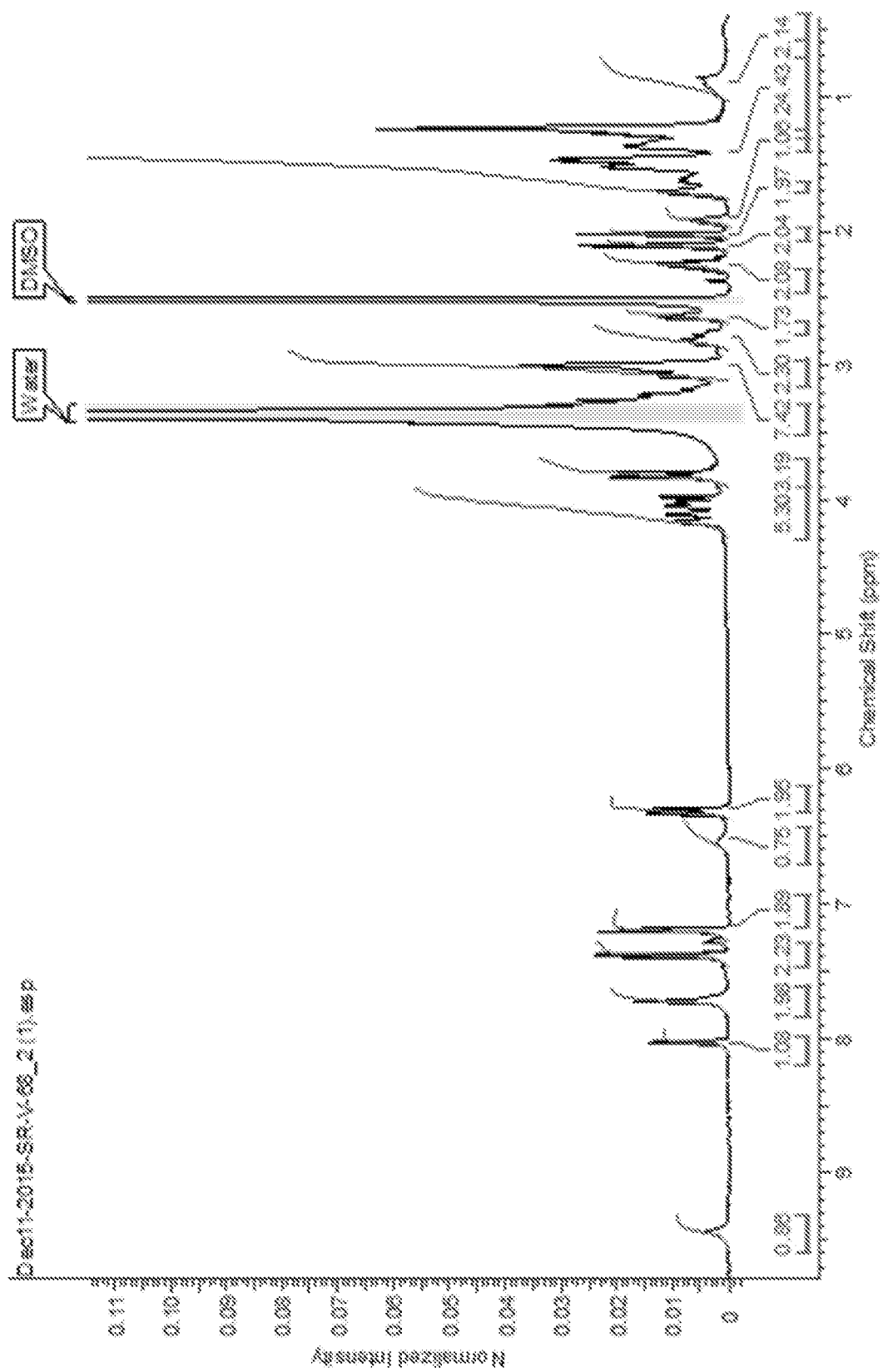
Figure 5A:
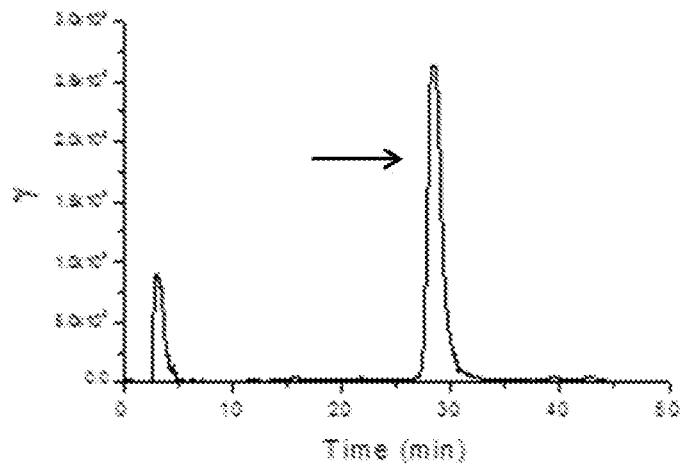
Figure 5B:
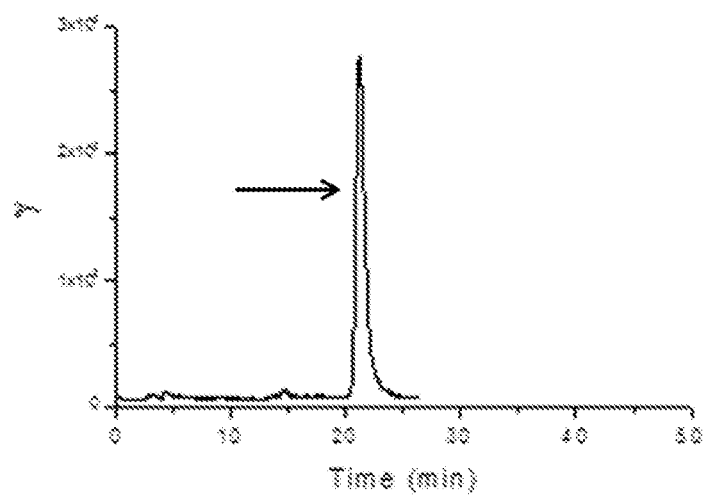
Figure 5C:
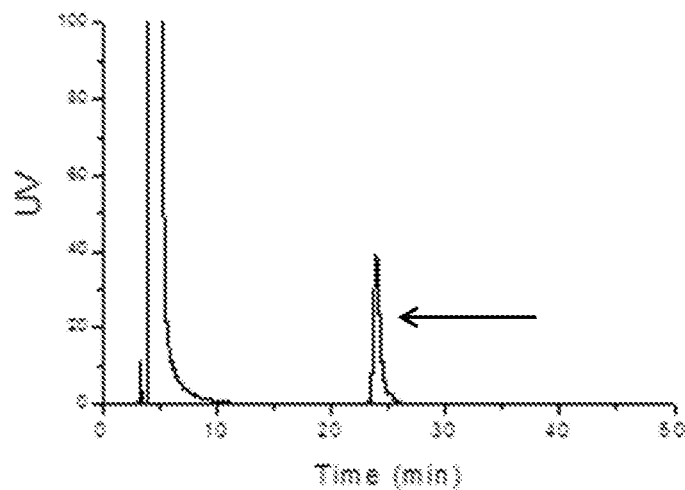
Figure 5D:
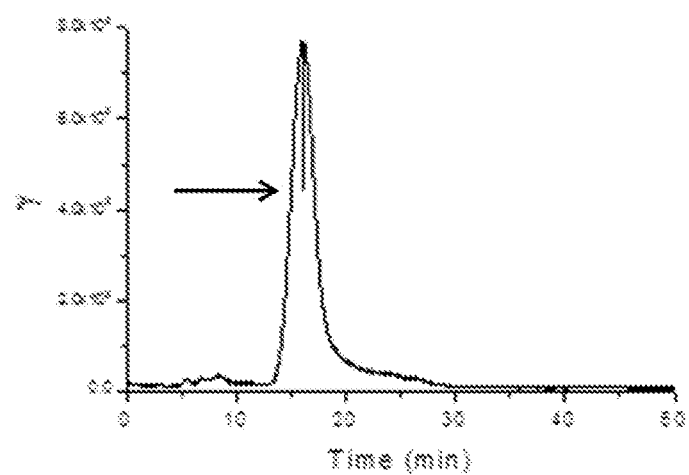
Figure 5E:
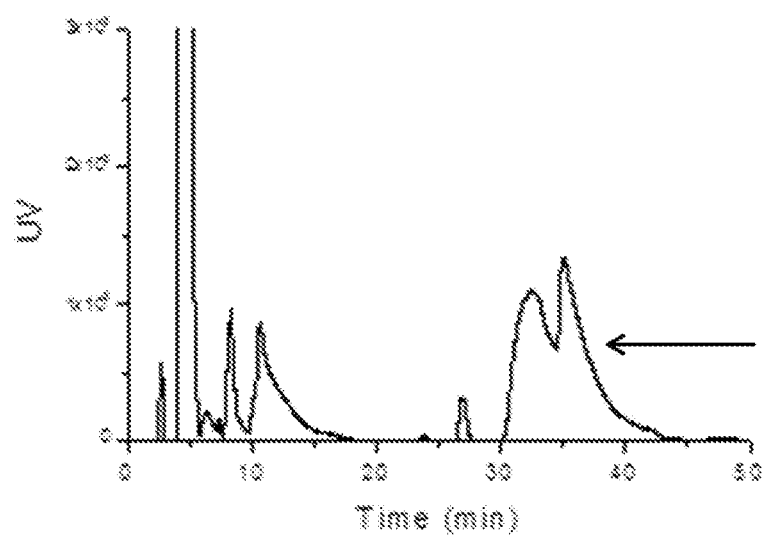
Figure 6:
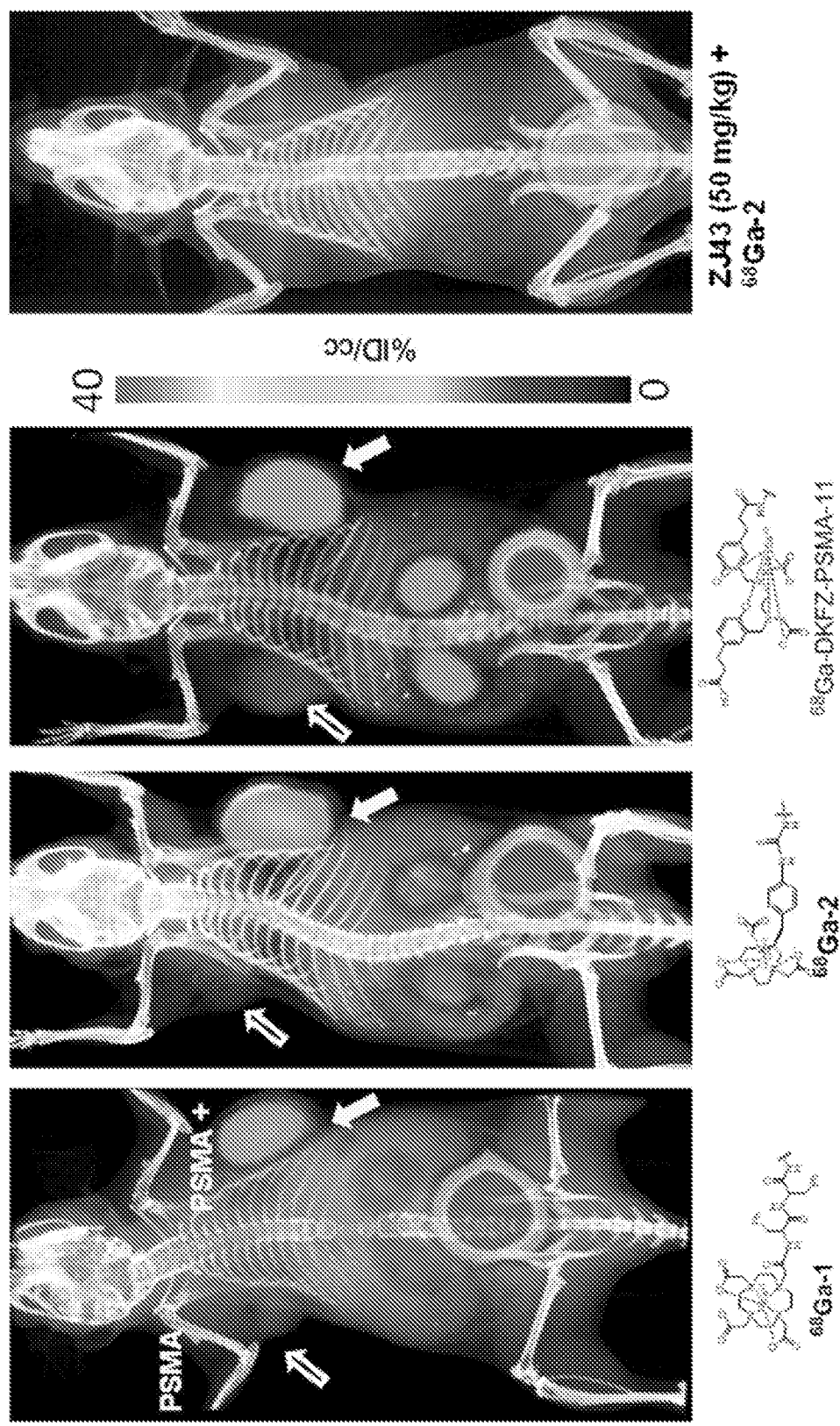

Having thus described the presently disclosed subject matter in general terms, reference will now be made to the accompanying Figures, which are not necessarily drawn to scale, and wherein:

FIG. 1 shows chemical structures of representative radiotracers used for the presently disclosed studies;

FIG. 2A, FIG. 2B, FIG. 2C, and FIG. 2D show the comparison of selected tissue uptake of $^{68}$Ga-1, $^{68}$Ga-2 and $^{68}$Ga-DKFZ-PSMA-11 in male SCID-NOD mice (n=4) bearing both PSMA+ PC3 PIP and PSMA− PC3 flu tumors: (A) PSMA+ PC3 PIP tumor; (B) kidney; (C) salivary gland; and (D) spleen; (*, P<0.05; , P<0.001; *, P<0.0001;

FIG. 3A, FIG. 3B, FIG. 3C, and FIG. 3D show the comparison of PSMA+ PC3 PIP tumor-to-PSMA− PC3 flu tumor (A); PSMA+ PC3 PIP-to-kidney (B); PSMA+ PC3 PIP-to-salivary gland (C); and, PSMA+ PC3 PIP-to-blood (D) of $^{68}$Ga-1, $^{68}$Ga-2 and $^{68}$Ga-DKFZ-PSMA-11; (*, P<0.05; , P<0.001; *, P<0.0001);

FIG. 4 shows the $^1$H NMR spectrum of Ga-2 in DMSO at room temperature;

FIG. 5A, FIG. 5B, FIG. 5C, FIG. 5D, and FIG. 5E show preparative HPLC chromatograms of $^{68}$Ga-1 (A), $^{68}$Ga-2 (B, C) and $^{68}$Ga-DKFZ-PSMA-11 (D, E) for radio-HPLC (A,B, D) and UV (C, E) peaks; and FIG. 6 shows whole-body PET-CT imaging at 1 h post injection for the radiotracers, $^{68}$Ga-1, $^{68}$Ga-2 and $^{68}$Ga-DKFZ-PSMA-11 using NOD-SCID male mice bearing both PSMA+ PC3 PIP (right) and PSMA− flu (left) tumor xenografts within the upper flanks; PSMA+ PC3 tumor uptake for $^{68}$Ga-2 was further blocked by injecting ZJ43 (50 mg/kg), 30 min prior to injection of the radiotracer.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the particular embodiments disclosed and that modifications and other embodiments are intended to be included within the scope of the appended claims.

I. $^{68}$Ga-Labeled Nota-Chelated PSMA-Targeted Imaging and Therapeutic Agents

Prostate-specific membrane antigen (PSMA) is an increasingly important target for imaging and therapy of prostate cancer. A variety of high affinity radiohalogenated, urea-based PSMA inhibitors that selectively image prostate tumors in experimental models has been previously synthesized. Chelated radiometal-linker-urea conjugates also have been synthesized. These compounds also selectively image prostate tumors in experimental models. $^{68}$Ga-Labeled, low-molecular-weight imaging agents that target the prostate-specific membrane antigen (PSMA) are increasingly used clinically to detect prostate and other cancers with positron emission tomography (PET). The DOTA ligand was selected because it can chelate both imaging and therapeutic nuclides. The growing number of clinical trials employing $^{68}$Ga-based, PSMA-targeted PET has encouraged the investigation of structural elements that could promote the least off-target uptake of this class of radiotracers.

Accordingly, the presently disclosed subject matter provides, in some embodiments, a head-to-head, preclinical comparison of radiometal-chelate-linker-urea based PSMA binding imaging agents, wherein the chelating agents are DOTA (1,4,7,10-tetraazacyclododecane-1,4,7,10-tetraacetic acid) and NOTA (1,4,7-triazacyclononane-1,4,7-trisacetic acid), with a known imaging agent, DKFZ-PSMA-11, when radiolabeled with $^{68}$Ga.

More particularly, the presently disclosed subject matter, in some embodiments, directly compares the tumor uptake, selectivity and pharmacokinetics of a known radiotracer, $^{68}$Ga-1, the presently disclosed, $^{68}$Ga-2, which in contrast to $^{68}$Ga-1, employs the NOTA chelator, and $^{68}$Ga-DKFZ-PSMA-11, which is currently in imaging clinical trials for prostate cancer agent. Specific attention was given to decrease activity within renal and salivary gland tissue, commonly seen with these agents. It is believed that a preclinical study such as this retains value as it is carefully controlled and all of the aforementioned agents were evaluated for pharmacokinetics in preclinical studies (Banerjee et al. (2010) *J Med Chem* 53, 5333-41; Eder et al. (2012) *Bioconjug Chem* 23, 688-97)—with similar comparisons performed—before their successful move to the clinic (Eder et al. (2012) *Bioconjug Chem* 23, 688-97; Weineisen et al. (2014) *EJNMMI Res* 4, 63).

The preparation and use of PSMA binding ureas conjugated to chelated radiometals via various linking groups for imaging and possible radiotherapy of PSMA expressing tumors has been described. Institute, N. C. Cancer Statistics (2015); Afshar-Oromieh et al., (2014) *Eur J Nucl Med Mol Imaging*; Afshar-Oromieh et al., (2013) *Eur J Nucl Med Mol Imaging*, 40, 486-95; Murphy et al., (1995) *Prostate*, 26, 164-8; Murphy et al., (1998) *Urology*, 51, 89-97; and Murphy et al., (1998) *J Urol*, 160, 2396-401. See also, international PCT patent application publication nos. WO 2009/002529 A2 and WO2010/108125A2, each of which is incorporated herein by reference in their entirety.

In the presently disclosed subject matter, $^{68}$Ga-1, which is disclosed in WO 2010108125 A2 20100923, and the new radiotracer $^{68}$Ga-2 were compared with $^{68}$Ga-DKFZ-PSMA-11, which is currently in clinical trial in Europe. Structures of the representative agents are shown in FIG. 1.

The precursors for the agents $^{68}$Ga-1 and $^{68}$Ga-2 were reported earlier, Banerjee, et al., *J. Medicinal Chem.* (2010); Banerjee, et al., *J. Med. Chem.* (2014), although no $^{68}$Ga agent has been reported. In vivo biological properties of the presently disclosed agents are disclosed herein, demonstrating superior biodistribution properties in comparison to $^{68}$Ga-DKFZ-PSMA-11. See Eder et al., *Bioconjugate chemistry* (2012).

A. Compounds of Formula (I)

Accordingly, in some embodiments, the presently disclosed subject matter provides a compound of Formula (I):

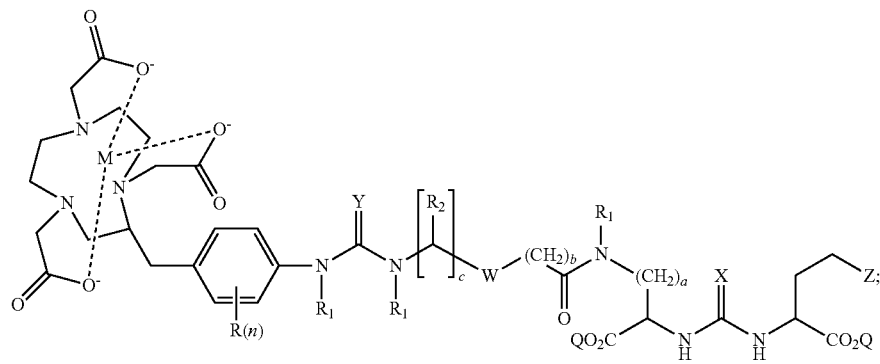

(I)

wherein: Z is tetrazole or $CO_2Q$; Q is H or a protecting group; X and Y are each independently O or S; a is an integer selected from the group consisting of 1, 2, 3 and 4; b and c are each independently an integer selected from the group consisting of 0, 1, 2, 3, 4, 5, 6, 7, 8, 9, and 10; W is selected from the group consisting of —C(=O)—$NR_4$—, —$NR_4$—C(=O)—, —$NR_4$C(=O)—$NR_4$—, —$NR_4$—C(=S)—$NR_4$—, —$NR_4$—C(=O)—O—, —O—C(=O)—$NR_4$—, —O—C(=O)—, and —C(=O)—O—; each $R_1$ is independently H or $C_1$-$C_4$ alkyl; each $R_2$ is independently H or —$COOR_3$, wherein each $R_3$ is independently H or a $C_1$-$C_6$ alkyl; each $R_4$ is independently H or $C_1$-$C_4$ alkyl; each R is independently selected from the group consisting of hydrogen, halogen, alkyl, alkenyl, alkynyl, aryl, heteroaryl, alkyaryl, arylakyl, and alkylheteroaryl; n is an integer selected from the group consisting of 0, 1, 2, 3 and 4; and M is a metal; and pharmaceutically acceptable salts thereof.

Formula (I) does not include compounds disclosed in WO 2009/002529 and WO 2010/108125.

In particular embodiments of the compound of Formula (I), the metal (M) is selected from the group consisting of Tc-94m, Tc-99m, In-111, Ga-67, Ga-68, Y-86, Y-90, Lu-177, Re-186, Re-188, Cu-64, Cu-67, Co-55, Co-57, Sc-47, Ac-225, Bi-213, Bi-212, Pb-212, Sm-153, Ho-166, Gd-152, or Dy-166.

In yet more particular embodiments, the metal (M) is Ga-68.

In still more particular embodiments, the compound of Formula (I) is $^{68}$Ga-SRVI68.

B. Methods of Using Compounds of Formula (I) for Imaging One or More PSMA-Expressing Tumors or Cells In other embodiments, the presently disclosed subject matter provides a method for imaging one or more prostate-specific membrane antigen (PSMA) tumors or cells, the method comprising contacting to the one or more tumors or cells, with an effective amount of a compound of Formula (I) and making an image, the compound of Formula (I) comprising:

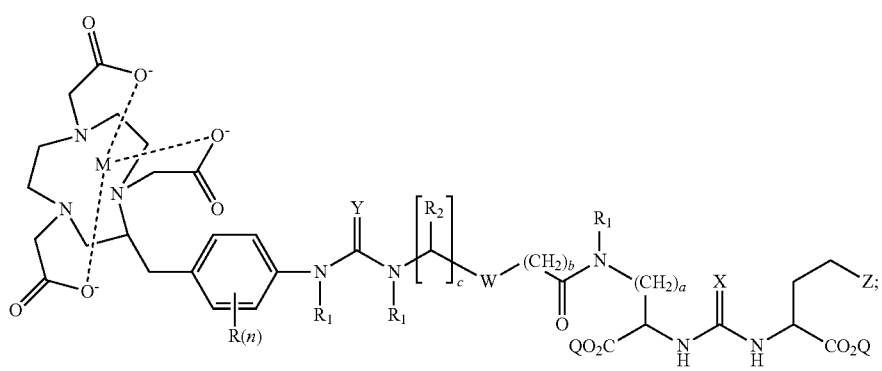

(I)

wherein: Z is tetrazole or $CO_2Q$; Q is H or a protecting group; X and Y are each independently O or S; a is an integer selected from the group consisting of 1, 2, 3 and 4; b and c are each independently an integer selected from the group consisting of 0, 1, 2, 3, 4, 5, 6, 7, 8, 9, and 10; W is selected from the group consisting of —C(=O)—$NR_4$—, —$NR_4$—C(=O)—, —$NR_4$C(=O)—$NR_4$—, —$NR_4$—C(=S)—$NR_4$—, —$NR_4$—C(=O)—O—, —O—C(=O)—$NR_4$—, —O—C(=O)—, and —C(=O)—O—; each $R_1$ is independently H or $C_1$-$C_4$ alkyl; each $R_2$ is independently H or —$COOR_3$, wherein each $R_3$ is independently H or a $C_1$-$C_6$ alkyl; each $R_4$ is independently H or $C_1$-$C_4$ alkyl; each R is independently selected from the group consisting of hydrogen, halogen, alkyl, alkenyl, alkynyl, aryl, heteroaryl, alkyaryl, arylakyl, and alkylheteroaryl; n is an integer selected from the group consisting of 0, 1, 2, 3 and 4; and M is a radioactive metal suitable for imaging; and pharmaceutically acceptable salts thereof.

Formula (I) does not include compounds disclosed in WO 2009/002529 and WO 2010/108125.

"Contacting" means any action which results in at least one compound comprising the imaging agent of the presently disclosed subject matter physically contacting at least one PSMA-expressing tumor or cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route.

According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and cell(s) or tumor(s).

By "making an image", it is meant using positron emission tomography (PET) or single-photon emission computed tomography (SPECT) imaging to form an image of a cell, tissue, tumor, part of body, and the like. The presently disclosed methods include radioactive metal capable of emitting radiation suitable for detection with PET or SPECT.

In some embodiments, the radioactive metal suitable for imaging (M) is selected from the group consisting of Tc-94m, Tc-99m, In-111, Ga-67, Ga-68, Y-86, Y-90, Lu-177, Re-186, Re-188, Cu-64, Cu-67, Co-55, Co-57, Sc-47, Ac-225, Bi-213, Bi-212, Pb-212, Sm-153, Ho-166, Gd-152, or Dy-166. In particular embodiments, the radioactive metal suitable for imaging (M) is Ga-68. In more particular embodiments, the compound of Formula (I) is $^{68}$Ga-2.

In some embodiments, the imaging comprises positron emission tomography (PET). In other embodiments, the imaging comprises single-photon emission computed tomography (SPECT).

In some embodiments, the one or more PSMA-expressing tumors or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In particular embodiments, the one or more PSMA-expressing tumors or cells is a prostate tumor or cell.

In other embodiments, the one or more PSMA-expressing tumors or cells is in vitro, in vivo or ex-vivo. In yet other embodiments, the one or more PSMA-expressing tumors, cells organs, or tissues is present in a subject.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In some embodiments, a detectably effective amount of the imaging agent of the presently disclosed methods is administered to a subject. In accordance with the presently disclosed subject matter, "a detectably effective amount" of the imaging agent is defined as an amount sufficient to yield an acceptable image using equipment which is available for clinical use. A detectably effective amount of the imaging agent may be administered in more than one injection. The detectably effective amount of the imaging agent can vary according to factors such as the degree of susceptibility of the individual, the age, sex, and weight of the individual, idiosyncratic responses of the individual, the dosimetry, and instrument and film-related factors. Optimization of such factors is well within the level of skill in the art. In some embodiments, the compound of formula (I) comprising the radioactive metal suitable for imaging substantially localizes to the tumor or cell within about 60 minutes of administration.

It is preferable that the compounds of the presently disclosed subject matter are excreted from tissues of the body quickly. In some embodiments, the presently disclosed methods comprise clearance of the compound comprising the imaging agent from the tumor or cell in the subject. In some other embodiment, the imaging agent is cleared more rapidly from a subject's kidneys than from a tumor in the subject.

C. Methods of Using Compounds of Formula (I) for Treating a Disease or Condition Associated with One or More One or More PSMA-Expressing Tumors or Cells In other embodiments, the presently disclosed subject matter provides a method for treating or preventing a disease or condition associated with one or more PSMA expressing tumors or cells, the method comprising administering to a subject in need of treatment thereof, at least one compound of Formula (I), in an amount effective to treat or prevent the disease or condition, the compound of formula (I) comprising:

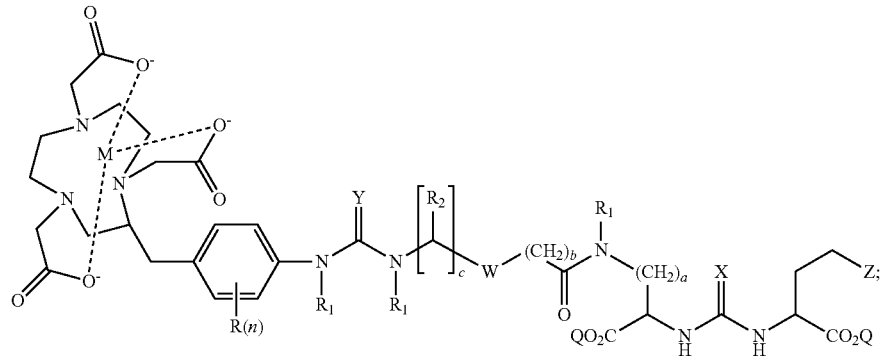

(I)

wherein: Z is tetrazole or $CO_2Q$; Q is H or a protecting group; X and Y are each independently O or S; a is an integer selected from the group consisting of 1, 2, 3 and 4; b and c are each independently an integer selected from the group consisting of 0, 1, 2, 3, 4, 5, 6, 7, 8, 9, and 10; W is selected from the group consisting of —C(=O)—NR$_4$—, —NR$_4$—C(=O)—, —NR$_4$C(=O)—NR$_4$—, —NR$_4$—C(=S)—NR$_4$—, —NR$_4$—C(=O)—O—, —O—C(=O)—NR$_4$—, —O—C(=O)—, and —C(=O)—O—; each $R_1$ is independently H or alkyl; each $R_2$ is independently H or —COOR$_3$, wherein each $R_3$ is independently H or a $C_1$-$C_6$ alkyl; each $R_4$ is independently H or C alkyl; each R is independently selected from the group consisting of hydrogen, halogen, alkyl, alkenyl, alkynyl, aryl, heteroaryl, alkyaryl, arylakyl, and alkylheteroaryl; n is an integer selected from the group consisting of 0, 1, 2, 3 and 4; and M is a radioactive metal suitable for radiotherapy; and pharmaceutically acceptable salts thereof.

Formula (I) does not include compounds disclosed in WO 2009/002529 and WO 2010/108125.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

In general, the "effective amount" of an active agent refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of Formula (I) and at least one other active agent. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

In particular embodiments, the disease or condition is a prostate cancer, renal cancer, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, adenomas, and tumor neovasculature. In more particular embodiments, the disease or condition is prostate cancer. Accordingly, the presently disclosed compounds can be administered prophylactically to prevent or reduce the incidence or recurrence of the cancer or the tumor neovasculature.

A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within a subject, or circulate in the blood stream as independent cells, for example, leukemic cells.

A cancer can include, but is not limited to, renal cancer, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. In more particular embodiments, the disease or condition is prostate cancer. In some embodiments, a detectably effective amount of the therapeutic agent of the presently disclosed methods is administered to a subject.

D. Kits

In yet other embodiments, the presently disclosed subject matter provides a kit comprising a compound of Formula (I). Formula (I) does not include compounds disclosed in WO 2009/002529 and WO 2010/108125.

In certain embodiments, the kit provides packaged pharmaceutical compositions comprising a pharmaceutically acceptable carrier and a compound of the invention. In certain embodiments the packaged pharmaceutical composition will comprise the reaction precursors necessary to generate the compound of the invention upon combination with a radio labeled precursor. Other packaged pharmaceutical compositions provided by the present invention further comprise indicia comprising at least one of: instructions for preparing compounds according to the invention from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

E. Pharmaceutical Compositions and Administration

In another aspect, the present disclosure provides a pharmaceutical composition including one compounds of Formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, acylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —CH$_2$CH$_2$CH$_2$CH$_2$—, —CH$_2$CH=CHCH$_2$—, —CH$_2$C≡CCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxy (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

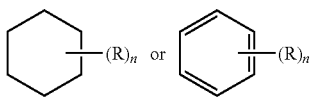

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

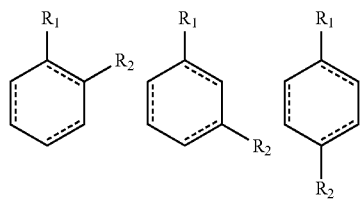

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ~~~~ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl. "Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C— or $^{14}$C— enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Overview $^{68}$Ga-Labeled, low-molecular-weight imaging agents that target the prostate-specific membrane antigen (PSMA) are increasingly used clinically to detect prostate and other cancers with positron emission tomography (PET). The presently disclosed subject matter compares the pharmacokinetics of three PSMA-targeted radiotracers: $^{68}$Ga-1, using DOTA-monoamide as the chelating agent; $^{68}$Ga-2, containing the macrocyclic chelating agent p-SCN-Bn-NOTA, and $^{68}$Ga-DKFZ-PSMA-11, currently in clinical trials, which uses the acyclic chelating agent, HBED-CC. The PSMA-targeting scaffold for all three agents utilizes a similar Glu-Lys-urea-linker construct. Each radiotracer enabled visualization of PSMA+ PC3 PIP tumor, kidney, and urinary bladder as early as 15 min post-injection using small animal PET/computed tomography (PET/CT). $^{68}$Ga-2 demonstrated the highest PSMA+ PC3 PIP tumor uptake, at 42.2±6.7 percentage injected dose per gram (% ID/g) of tissue at 1 h post-injection, and the fastest rate of clearance from all tissues. $^{68}$Ga-1 and $^{68}$Ga-DKFZ-PSMA-11 displayed similar uptake and retention patterns in PSMA+ PC3 PIP tumors up to 3 h post-injection. $^{68}$Ga-DKFZ-PSMA-11 demonstrated the highest uptake and retention in normal tissues, including kidney, blood, spleen, salivary glands and PSMA-negative PC3 flu tumors up to 3 h post-injection. In this preclinical evaluation $^{68}$Ga-2 had the most advantageous characteristics for PSMA-targeted PET imaging. The biodistribution profile of $^{68}$Ga-1 indicates promise for future therapeutic radionuclides that could employ a similar combination of chelator and targeting scaffold.

Example 2

Material and Methods

Solvents and chemicals purchased from commercial sources were of analytical grade or better and used without further purification. [$^{68}$Ga]GaCl$_3$ was obtained from the University of Wisconsin. DOTA-tris(t-butyl ester)-monoacid and p-SCN-Bn-NOTA were received from Macrocyclics, Inc. (Dallas, Tex.). Compounds 1 and 2 were synthesized following our previous report (Banerjee et al. (2010) *J Med Chem* 53, 5333-41). DKFZ-PSMA-11 and the corresponding stable Ga-DKFZ-PSMA-11 were purchased from ABX (Radeberg, Germany). Triethylsilane (Et$_3$SiH), diisopropylethylamine (DIEA) and triethylamine (TEA) were purchased from Sigma-Aldrich (St. Louis, Mo.). All other chemicals were purchased from Thermo Fisher Scientific (Pittsburgh, Pa.) unless otherwise specified.

Analytical thin-layer chromatography (TLC) was performed using Aldrich aluminum-backed 0.2 mm silica gel Z19, 329-1 plates and was visualized by ultraviolet light (254 nm), I$_2$ and 1% ninhydrin in EtOH. Flash chromatography was performed using silica gel (MP SiliTech 32-63 D 60 Å) purchased from Bodman (Aston, Pa.). All in vitro PSMA binding studies and determination of partition coefficients were performed in triplicate to ensure reproducibility, as previously reported (Banerjee et al. (2011) *Angewandte Chemie* 50, 9167-70). $^1$H NMR spectra were recorded on a Bruker Ultrashield™ 400 MHz spectrometer. Chemical shifts (δ) are reported in ppm downfield in reference to proton resonances resulting from incomplete deuteration of the NMR solvent. Quantitative $^1$H NMR was used to prove that all synthesized compounds were at >95% chemical purity.

Low resolution ESI mass spectra were obtained on a Bruker Daltonics Esquire 3000 Plus spectrometer. High resolution mass spectra were obtained by the University of Notre Dame Mass Spectrometry & Proteomics Facility, Notre Dame, Ind., using electrospray ionization (ESI) mass spectrometry either by direct infusion on a Bruker microTOF-II or by LC elution via an ultra-high pressure Dionex RSLC C$_{18}$ column coupled to a Bruker microTOF-Q II. The purity of tested compounds was also determined by analytical high performance liquid chromatography (HPLC) with absorbance at 220 nm and were all again determined to be >95%.

HPLC purification of stable compounds was performed using a Phenomenex C$_{18}$ Luna 10×250 mm$^2$ column and elution with water (0.1% TFA) (A) and CH$_3$CN (0.1% TFA) (B) on a Waters 600E Delta LC system with a Waters 486 variable wavelength UV/Vis detector, both controlled by Empower software (Waters Corporation, Milford, Mass.). HPLC purifications of $^{68}$Ga-1, $^{68}$Ga-2 and $^{68}$Ga-DKFZ-PSMA-11 were performed on a Varian Prostar System (Palo Alto, Calif.), equipped with a Varian ProStar 325 UV-Vis variable wavelength detector and a Bioscan Flow-count in-line Radioactivity detector (Washington D.C.), all controlled by Galaxie software (Varian Inc., Walnut Creek, Calif.).

All radiotracers were purified using a Varian microsob-MV 100-5 $C_8$ 25×4.6 mm column with a flow rate 1 mL/min with water (0.1% TFA) (A) and $CH_3CN$ (0.1% TFA) (B) as the eluting solvents. In order to ensure uniform purity of the compounds undergoing comparison, various HPLC methods were applied to separate excess ligand from the radiolabeled compound. For $^{68}$Ga-1, an isocratic solution of 80% A and 20% B was used. For $^{68}$Ga-2 and $^{68}$Ga-DKFZ-PSMA-11, an isocratic solution of 85% water and 15% B was employed.

Retention times of the radiolabeled compound and unlabeled free ligands are listed in Table 1. The radiochemical yield and purity of the radiotracers were further checked by withdrawing 1 μL aliquots of the radiolabeled solution and were analyzed by radio-TLC on RP-18 thin layer plates using 5/1 saline/methanol as the mobile phase. The specific radioactivity was calculated as the radioactivity eluting at the retention time of product during the preparative HPLC purification divided by the mass corresponding to the area under the curve of the UV absorption.

Radiolabeling Methods.

$^{68}$Ga-Labeling of target ligands was performed according to a method previously reported (Banerjee et al. (2010) *J Med Chem* 53, 5333-41) and following other literature procedures (Eder et al. (2012) *Bioconjug Chem* 23, 688-97; Zhernosekov et al. (2007) *J Nucl Med* 48, 1741-8. Briefly, 488 MBq (13 mCi) of $^{68}$GaCl$_3$ in 7 mL of 0.1 N HCl were obtained from an 18-month-old 1,850 MBq (50 mCi) $^{68}$Ge/$^{68}$Ga generator, Eckert-Ziegler (Berlin, Del.). Pre-concentration was performed on a cation-exchange cartridge. The purified $^{68}$Ga(III)Cl$_3$ was obtained in a total volume of 400 μL, eluted in 2.4/97.6 0.05 N HCl/acetone. The $^{68}$Ga(III) in HCl/acetone was used immediately for the radiolabeling of 1, 2 or DKFZ-PSMA-11.

Two radiolabeling techniques were investigated. The first was undertaken in water (without any added buffer solution), as reported earlier (Banerjee et al. (2010) *J Med Chem* 53, 5333-41), and the second used 2.1 M HEPES buffer at pH about 4, as reported by Eder et al. (Eder et al. (2012) *Bioconjug Chem* 23, 688-97). Using HEPES buffer, each ligand (12.5 μg), was radiolabeled in >95% yield in a total volume of about 120 μL, however this yield was dependent on the total volume of the radiolabeling solution. In water the pre-concentrated $^{68}$Ga(III)Cl$_3$ solution could be directly used for radiolabeling at pH about 3-4 (Banerjee et al. (2010) *J Med Chem* 53, 5333-41). The total volume of the radiolabeling solution was about 300-350 μL to produce >93% yield using about 4-6 μg of each precursor ligand.

In a typical reaction 50 μL of the concentrated radioactivity was added to 250 μL of deionized H$_2$O in a 1.5 mL polypropylene vial, followed by addition of 3-5 μL of a solution of precursor ligand (2 μg/4 in water, pH about 3.5-4). The reaction vial was heated at 95° C. for 10 min for ligand 1, about 3 min for ligand 2 and the complex was allowed to form at room temperature for 10 min for both 2 and DKFZ-PSMA-11. Complex formation was monitored by iTLC as above, using 5/1 saline/methanol.

For the comparison studies, all three radiotracers were purified by HPLC to remove excess precursor ligand so that all three radioligands could be obtained in >98% purity. The acidic eluate was neutralized with 50 μL 1 M Na$_2$CO$_3$ and the volume of the eluate was reduced under vacuum to dryness. The solid residue was diluted with saline to the desired radioactivity concentration for biodistribution and imaging studies.

PSMA Inhibition Assay.

The PSMA inhibitory activity of 1, 2 and DKFZ-PSMA-11 and the corresponding natural Ga-labeled analogs Ga-1 and Ga-2 were determined using a fluorescence-based assay according to a previously reported procedure (Banerjee et al. (2011) *Angewandte Chemie* 50, 9167-70) (Table 1). Briefly, lysates of LNCaP cell extracts (25 μL) were incubated with the inhibitor (12.5 μL) in the presence of 4 μM N-acetylaspartylglutamate (NAAG) (12.5 μL) for 2 h. The amount of the glutamate released by NAAG hydrolysis was measured by incubating with a working solution (50 μL) of the Amplex Red Glutamic Acid Kit (Life Technologies, Grand Island, N.Y.) for 1 h.

Fluorescence was measured with a VICTOR3V multilabel plate reader (Perkin Elmer Inc., Waltham, Mass.) with excitation at 490 nm and emission at 642 nm. Inhibition curves were determined using semi-log plots and IC$_{50}$ values were determined at the concentration at which enzyme activity was inhibited by 50%. Enzyme inhibitory constants ($K_i$ values) were generated using the Cheng-Prusoff conversion (Cheng et al. (1973) *Biochemical pharmacology* 22, 3099-108). Assays were performed in triplicate. Data analysis was performed using GraphPad Prism version 4.00 for Windows (GraphPad Software, San Diego, Calif.).

Cell Lines.

Sublines of the androgen-independent PC3 human prostate cancer cell line, originally derived from an advanced androgen independent bone metastasis, were used. Those sublines have been modified to express high levels of PSMA [PSMA-positive (+) PC3 PIP] or are devoid of target [PSMA-negative (−) PC3 flu]. They were generously provided by Dr. Warren Heston (Cleveland Clinic). Cells were grown in RPMI 1640 medium (Corning Cellgro, Manassas, Va.) containing 10% fetal bovine serum (FBS) (Sigma-Aldrich, St. Louis, Mo.) and 1% penicillin-streptomycin (Corning Cellgro, Manassas, Va.). PSMA+ PC3 PIP cells were grown in the presence of 20 μg/mL of puromycin to maintain PSMA expression. All cell cultures were maintained in an atmosphere containing 5% carbon dioxide (CO$_2$), at 37.0° C. in a humidified incubator.

Tumor Models.

Animal studies were undertaken in compliance with the regulations of the Johns Hopkins University Animal Care and Use Committee. Six- to eight-week-old male, Nonobese Diabetic (NOD)/Severe Combined immunodeficient (SCID) mice (Johns Hopkins Immune Compromised Animal Core) were implanted subcutaneously (sc) with PSMA+ PC3 PIP and PSMA− PC3 flu cells (1×10$^6$ in 100 μL of HBSS (Corning Cellgro, Manassas, Va.) at the forward right and left flanks, respectively. Mice were imaged or used in biodistribution assays when the xenografts reached 5 to 7 mm in diameter.

Small-Animal PET Imaging and Analysis.

Whole-body PET and CT images were acquired on a SuperArgus PET-CT preclinical imaging system (SEDECAL SA4R PET-CT, Madrid, Spain). For imaging studies, mice were anesthetized with 3% and maintained under 1.5% isoflurane (v/v). PET-CT Imaging studies were performed on NOD/SCID mice bearing PSMA+ PC3 PIP and PSMA− PC3 flu tumors. After intravenous injection of $^{68}$Ga-1, $^{68}$Ga-2 or $^{68}$Ga-DKFZ-PSMA-11, whole-body PET emission images (two bed positions, 15 min per position) were acquired at the indicated (30 min, 1 h, 2 h and 3 h) time points after injection of radiotracer.

For binding specificity studies, a mouse was subcutaneously administered a blocking dose of the known PSMA inhibitor ZJ43 (Olszewski et al. (2004) *Journal of neurochemistry* 89, 876-85) (50 mg/kg) at 30 min before the injection of $^{68}$Ga-2, and another mouse was injected with $^{68}$Ga-2 alone. A CT scan was acquired after each PET scan in 512 projections using a 50 keV beam for anatomic co-registration. PET emission data were corrected for decay and dead time and were reconstructed using the 3-dimensional ordered-subsets expectation maximization algorithm. Data were displayed and analyzed using AMIDE software (http://sourceforge.net/amide).

Biodistribution.

Mice bearing PSMA+ PC3 PIP and PSMA− PC3 flu xenografts were injected via the tail vein with 740 kBq (20 µCi) of $^{68}$Ga-1, $^{68}$Ga-2 and $^{68}$Ga-DKFZ-PSMA-11 in 150 µL of saline (n=4). At 1 h, 2 h, and 3 h post-injection, mice were sacrificed by cervical dislocation and the blood was immediately collected by cardiac puncture. The heart, lungs, liver, stomach, pancreas, spleen, fat, kidney, muscle, small and large intestines, urinary bladder, PSMA+ PC3 PIP and PSMA− PC3 flu tumors were collected. Each organ was weighed, and the tissue radioactivity was measured with an automated gamma counter (1282 Compugamma CS, Pharmacia/LKBNuclear, Inc., Mt. Waverly, Vic. Australia). The percentage of injected dose per gram of tissue (% ID/g) was calculated by comparison with samples of a standard dilution of the initial dose. All measurements were corrected for decay.

Data Analysis.

Data are expressed as mean±standard deviation (SD). Prism software (GraphPAD, San Diego, Calif.) was used to determine statistical significance. Statistical significance was calculated using a two-tailed Student's t test. A P-value≤0.05 was considered significant.

Example 3

Results

Chemical and Radiochemical Syntheses and Characterization.

Structures of the radioligands used for the study are shown in FIG. 1. Lys-Glu urea was used as the PSMA-targeting moiety in all cases. Selected physical properties of 1, 2 and the corresponding natural Ga-complexes are summarized in Table 1. Since NOTA is a hexadentate $N_3O_3$ macrocyclic chelator, [$^{68}$Ga(III)]$^2$ was expected produce a neutral compound (Broan et al. (1991) *J. Chem. Soc. Perkin Trans.* 2, 87-99.). DKFZ-PSMA-11 chelated with HBED-CC is reported to provide a uni-negative, hexadentate chelation ($N_2O_4$) to Ga(III), with two carboxylates and two phenolates (L'Eplattenier et al. (1967) *Journal of the American Chemical Society* 89; Zoller et al. (1992) *Journal of Nuclear Medicine* 33, 1366-1372; Eder et al. (2008) *European Journal of Nuclear Medicine and Molecular Imaging* 35, 1878-1886). All three radiotracers were synthesized in high radiochemical yield (about 95-99%) and purity (>98%), with specific radioactivity>168 GBq/µmol (4.05 mCi/µmol).

Two radiolabeling methods have been investigated, one in the presence of HEPES buffer as reported by Eder et al. (Eder et al. (2012) *Bioconjug Chem* 23, 688-97) and the other by a method reported by Banerjee et al. (Banerjee et al. (2010) *J Med Chem* 53, 5333-41) following the literature (Zhernosekov et al. (2007) *J Nucl Med* 48, 1741-8). For the latter method, pre-concentrated $^{68}$Ga(III)Cl$_3$ could be directly used for radiolabeling, without adjusting pH, and radiolabeling could be done in a total volume of 300-350 µL using as low as 4 µg of any of the three ligands. Based on the HPLC retention time (Table 1), the non-radiolabeled precursor DKFZ-PSMA-11 was the least hydrophilic, although, after radiolabeling, $^{68}$Ga-DKFZ-PSMA-11 became the most hydrophilic compound in the series.

TABLE 1

Selected physical properties of the presently disclosed agents.

| | Molar Mass (g/mol) | $K_i$(nM) | 95% CI of $K_i$ (nM) | HPLC (RP $C_8$) retention time (min) |
|---|---|---|---|---|
| 1 | 1284.4 | 0.70 | 0.42-1.16 | 19.2-19.8$^a$ |
| Ga-1 | 1352.5 | 0.33 | 0.17-0.66 | 21.8-23.8$^a$ |
| 2 | 1054.2 | 0.81 | 0.35-1.89 | 23.9-24.9$^b$ |
| Ga-2 | 1120.9 | 0.38 | 2.26-6.28 | 20.8-22.5$^b$ |
| DKFZ-PSMA-11 | 947.0 | 0.03 | 0.016-0.06 | 34.5-40.0$^b$ |
| Ga-DKFZ-PSMA-11 | 1013.7 | N.A. | N.A. | 14.5-20.0$^b$ |
| ZJ43 | 304.3 | 0.31 | 0.20-0.48 | N.A. |

Compounds 1 and 2 are the unlabeled agents containing DOTA-monoamide and NOTA-Bn-SCN chelating agents, respectively.
$^a$Isocratic solution of 80% A and 20% B.
$^b$Isocratic solution of 85% water and 15% B. Flow rate was 1 mL/min for both methods.

Precursor ligands and the corresponding stable metal-labeled compounds demonstrated high binding affinity to PSMA, with $K_i$ values ranging from 0.03 to 0.81 nM (Table 1). The known, high-affinity PSMA inhibitor ZJ43 (Olszewski et al. (2004) *Journal of neurochemistry* 89, 876-85) was used as a reference ligand and exhibited a $K_i$ of 0.31 nM (Table 1). DKFZ-PSMA-11 displayed the highest PSMA-binding affinity from the compounds tested in this comparative study, ten-fold higher than either of Ga-1 and Ga-2. In addition, based on HPLC data, it was observed that DKFZ-PSMA-11 is the most lipophilic in the series, although after complexation with gallium (III), the agent Ga-DKFZ-PSMA-11, is the most hydrophilic in the series. The order of hydrophilicity is Ga-DKFZ-PSMA-11>Ga-2>Ga-SR2.

Biodistribution.

Tables 2, 3 and 4 show the pharmacokinetics in selected organs for $^{68}$Ga-1, $^{68}$Ga-2 and $^{68}$Ga-DKFZ-PSMA-11, respectively. All compounds exhibited clear PSMA-dependent binding in PSMA+ PC3 PIP tumor xenografts. The tumor uptake for $^{68}$Ga-1 was 19.46±1.81% ID/g at 1 h, highest at 2 h (24.75±1.05% ID/g) and remained high at 3 h post-injection (19.46±5.12% ID/g) (Table 2). PSMA+ PC3 PIP-to-PSMA− PC3 flu tumor uptake ratios were 83.60±3.59 at 1 h and 148.75±16.43 at 2 h. The distribution within normal organs and tissues was also favorable, with low blood and normal tissue uptake and rapid clearance. The highest non-specific accumulation of radioactivity was observed in the kidneys, where uptake was expectedly high and peaked at 26.45±6.85% ID/g at 1 h and decreased to 11.88±0.99% ID/g by 2 h and remained roughly the same at 3 h post-injection.

TABLE 2

Tissue biodistribution of $^{68}$Ga-1 in mice bearing PSMA+ PC3 PIP and PSMA− PC3 flu tumors (n = 4). Values are expressed as mean ± SD.

| Tissue | 1 h | 2 h | 3 h |
|---|---|---|---|
| blood | 0.45 ± 0.05 | 0.25 ± 0.01 | 0.16 ± 0.03 |
| heart | 0.16 ± 0.03 | 0.10 ± 0.01 | 0.07 ± 0.02 |
| lung | 0.43 ± 0.03 | 0.21 ± 0.01 | 0.14 ± 0.04 |
| liver | 0.19 ± 0.03 | 0.17 ± 0.02 | 0.13 ± 0.02 |
| spleen | 1.03 ± 0.28 | 0.39 ± 0.04 | 0.40 ± 0.19 |
| kidney | 26.45 ± 6.85 | 11.88 ± 0.99 | 12.09 ± 5.56 |
| muscle | 0.14 ± 0.10 | 0.04 ± 0.00 | 0.03 ± 0.01 |
| small intestine | 0.17 ± 0.03 | 0.10 ± 0.00 | 0.08 ± 0.01 |
| salivary gland | 0.25 ± 0.03 | 0.16 ± 0.00 | 0.11 ± 0.02 |

TABLE 2-continued

Tissue biodistribution of $^{68}$Ga-1 in mice bearing PSMA+ PC3 PIP and PSMA− PC3 flu tumors (n = 4). Values are expressed as mean ± SD.

| Tissue | 1 h | 2 h | 3 h |
|---|---|---|---|
| PSMA+ PC3 PIP | 19.46 ± 1.81 | 24.75 ± 1.05 | 19.46 ± 5.12 |
| PSMA− PC3 flu | 0.23 ± 0.03 | 0.17 ± 0.01 | 0.16 ± 0.03 |
| PIP:flu | 83.60 ± 3.59 | 148.75 ± 16.43 | 122.32 ± 31.28 |
| PIP:kidney | 0.82 ± 0.25 | 2.09 ± 0.09 | 1.77 ± 0.60 |
| PIP:blood | 59.17 ± 24.48 | 100.91 ± 10.12 | 236.06 ± 235.66 |
| PIP:salivary gland | 76.91 ± 2.73 | 157.24 ± 2.55 | 172.83 ± 27.29 |

Table 3 shows the organ-related % ID/g of uptake for $^{68}$Ga-2. $^{68}$Ga-2 showed the highest PSMA-dependent tumor uptake with 42.18±6.66% ID/g at 1 h post-injection. Tumor uptake remained high, with faster clearance from 1 h to 2 h. The PSMA+ PC3 PIP-to-PSMA− PC3 flu tumor ratios were 109.82±21.61 at 1 h, 232.14±25.99 at 2 h and 182.27±14.59 at 3 h. Renal uptake for $^{68}$Ga-2 was highest at 1 h, 106.37±23.29% ID/g, much higher than that seen for $^{68}$Ga-1 and showed faster renal clearance, which decreased to 34.73±5.74% ID/g by 2 h post-injection. In addition, non-target organs, such as blood, heart, liver, spleen, stomach, pancreas, showed lower uptake 1% ID/g at 1 h, except for spleen) and faster clearance than for $^{68}$Ga-1.

TABLE 3

Tissue biodistribution of $^{68}$Ga-2 in mice bearing PSMA+ PC3 PIP and PSMA− PC3 flu tumors (n = 4). Values are expressed as mean ± SD.

| Tissue | 1 h | 2 h | 3 h |
|---|---|---|---|
| Blood | 0.38 ± 0.18 | 0.07 ± 0.02 | 0.09 ± 0.02 |
| heart | 0.23 ± 0.08 | 0.04 ± 0.01 | 0.04 ± 0.01 |
| lung | 1.00 ± 0.20 | 0.25 ± 0.02 | 0.23 ± 0.07 |
| liver | 0.52 ± 0.15 | 0.16 ± 0.01 | 0.16 ± 0.03 |
| spleen | 4.88 ± 0.68 | 0.79 ± 0.23 | 0.69 ± 0.11 |
| kidney | 106.37 ± 23.29 | 34.73 ± 5.74 | 12.68 ± 4.92 |
| muscle | 0.12 ± 0.02 | 0.03 ± 0.01 | 0.03 ± 0.02 |
| small intestine | 0.21 ± 0.08 | 0.04 ± 0.01 | 0.05 ± 0.02 |
| salivary gland | 0.23 ± 0.08 | 0.16 ± 0.11 | 0.08 ± 0.01 |
| PSMA+ PC3 PIP | 42.18 ± 6.66 | 21.66 ± 3.68 | 17.39 ± 5.55 |
| PSMA− PC3 flu | 0.40 ± 0.14 | 0.10 ± 0.01 | 0.09 ± 0.03 |
| PIP:flu | 109.82 ± 21.61 | 232.14 ± 25.99 | 182.27 ± 14.59 |
| PIP:kidney | 0.40 ± 0.06 | 0.67 ± 0.14 | 1.63 ± 0.05 |
| PIP:blood | 119.62 ± 28.54 | 320.90 ± 78.52 | 206.66 ± 32.95 |
| PIP:salivary gland | 188.14 ± 35.20 | 211.89 ± 2.83 | 222.32 ± 35.18 |

Table 4 lists the organ-related % ID/g of uptake for $^{68}$Ga-DKFZ-PSMA-11. Unlike $^{68}$Ga-1, $^{68}$Ga-DKFZ-PSMA-11 showed the highest PSMA-dependent tumor uptake with 26.86±5.59% ID/g at 3 h post-injection. Tumor uptake was nearly comparable from 1 to 3 h post-injection. The PSMA+ PC3 PIP-to-PSMA− PC3 flu ratios were 46.62±7.57% ID/g at 1 h, 57.68±27.10% ID/g at 2 h and 110.57±21.27% ID/g at 3 h post-injection.

TABLE 4

Tissue biodistribution of $^{68}$Ga-DKFZ-PSMA-11 in mice bearing PSMA+ PC3 PIP and PSMA− PC3 flu tumors (n = 4). Values are expressed as mean ± SD.

| Tissue | 1 h | 2 h | 3 h |
|---|---|---|---|
| blood | 0.75 ± 0.20 | 0.41 ± 0.06 | 0.34 ± 0.06 |
| heart | 0.42 ± 0.16 | 0.28 ± 0.06 | 0.20 ± 0.04 |
| lung | 2.21 ± 0.48 | 2.07 ± 0.68 | 1.26 ± 0.20 |
| liver | 0.75 ± 0.19 | 0.33 ± 0.05 | 0.38 ± 0.15 |
| spleen | 12.35 ± 3.75 | 8.87 ± 1.50 | 7.18 ± 2.25 |
| kidney | 133.24 ± 21.08 | 88.56 ± 20.09 | 119.54 ± 15.49 |
| muscle | 0.32 ± 0.12 | 0.19 ± 0.09 | 0.14 ± 0.02 |
| small intestine | 0.39 ± 0.09 | 0.19 ± 0.07 | 0.17 ± 0.06 |
| salivary gland | 1.42 ± 0.33 | 1.02 ± 0.22 | 0.86 ± 0.12 |
| PSMA+ PC3 PIP | 25.96 ± 9.69 | 21.08 ± 1.17 | 26.86 ± 5.59 |
| PSMA− PC3 flu | 0.57 ± 0.14 | 0.41 ± 0.17 | 0.25 ± 0.07 |
| PIP:flu | 46.62 ± 17.57 | 57.68 ± 27.10 | 110.57 ± 21.27 |
| PIP:kidney | 0.20 ± 0.09 | 0.24 ± 0.04 | 0.22 ± 0.04 |
| PIP:blood | 35.45 ± 13.43 | 51.88 ± 10.82 | 79.55 ± 9.83 |
| PIP:salivary gland | 18.57 ± 8.78 | 20.99 ± 3.40 | 31.40 ± 4.85 |

Figure 2A:
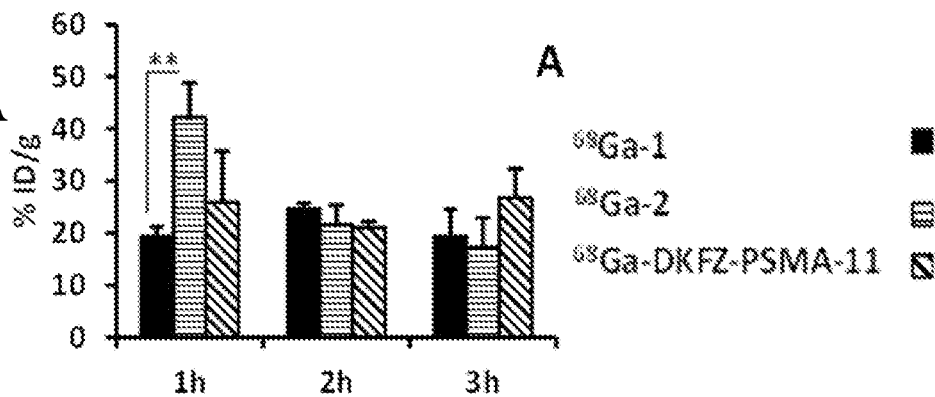

FIG. 2A, FIG. 2B, FIG. 2C and FIG. 2D summarize several comparative tissue uptake properties of the three agents. PSMA+ PC3 PIP tumor uptake of $^{68}$Ga-2 was significantly higher than $^{68}$Ga-1 at 1 h post-injection (P<0.004) (FIG. 2A). There was no significant difference in PSMA+ PIP tumor uptake between $^{68}$Ga-1 and $^{68}$Ga-DKFZ-PSMA-11 or between $^{68}$Ga-2 and $^{68}$Ga-DKFZ-PSMA-11 (P<0.09). In addition, there were no significant differences in tumor uptake at 2 h and 3 h post-injection between the compounds.

Figure 2B:
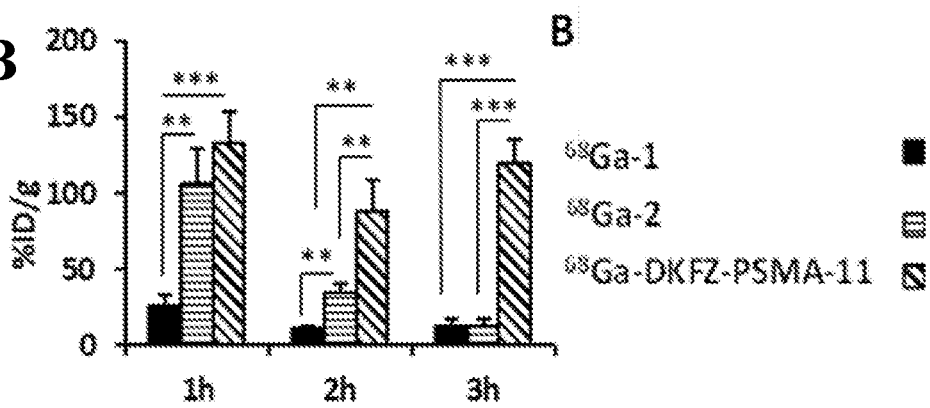

As shown in FIG. 2B, renal uptake of $^{68}$Ga-1 was significantly lower than $^{68}$Ga-2 (P<0.006) and $^{68}$Ga-DKFZ-PSMA-11 (P<0.001) at 1 h, although there was no significant difference between $^{68}$Ga-2 and $^{68}$Ga-DKFZ-PSMA-11. At 2 h post-injection renal uptake of both $^{68}$Ga-1 and $^{68}$Ga-2 were significantly lower than for $^{68}$Ga-DKFZ-PSMA-11 (P<0.003) and renal uptake of $^{68}$Ga-1 was still significantly lower than $^{68}$Ga-2 (P<0.005). At 3 h post-injection renal uptake of both $^{68}$Ga-1 and $^{68}$Ga-2 were significantly lower than for $^{68}$Ga-DKFZ-PSMA-11.

Figure 2C:
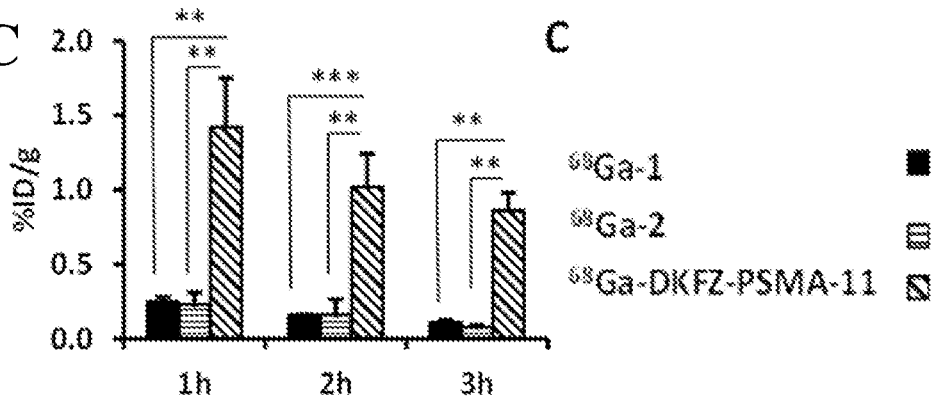

FIG. 2C reveals that $^{68}$Ga-DKFZ-PSMA-11 demonstrated significantly higher salivary gland uptake up to 3 h after injection compared to $^{68}$Ga-1 and $^{68}$Ga-2 (P<0.001).

Figure 2D:
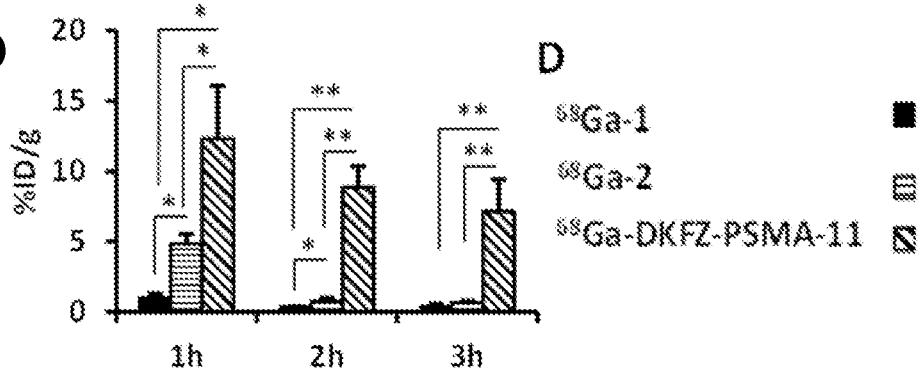
Figure 3A:
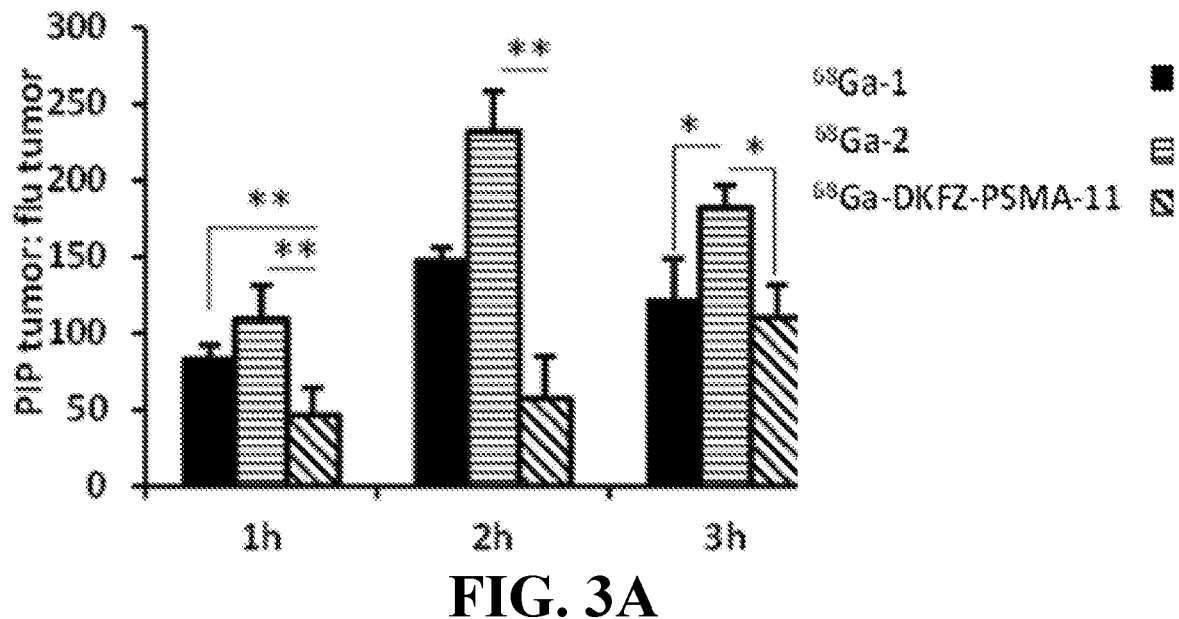
Figure 3B:
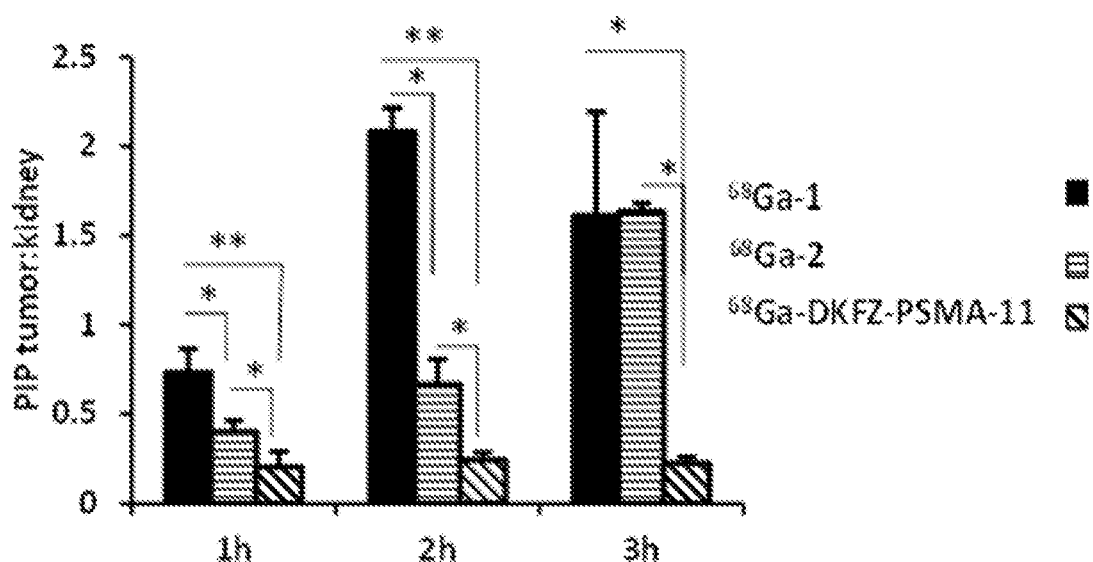
Figure 3C:
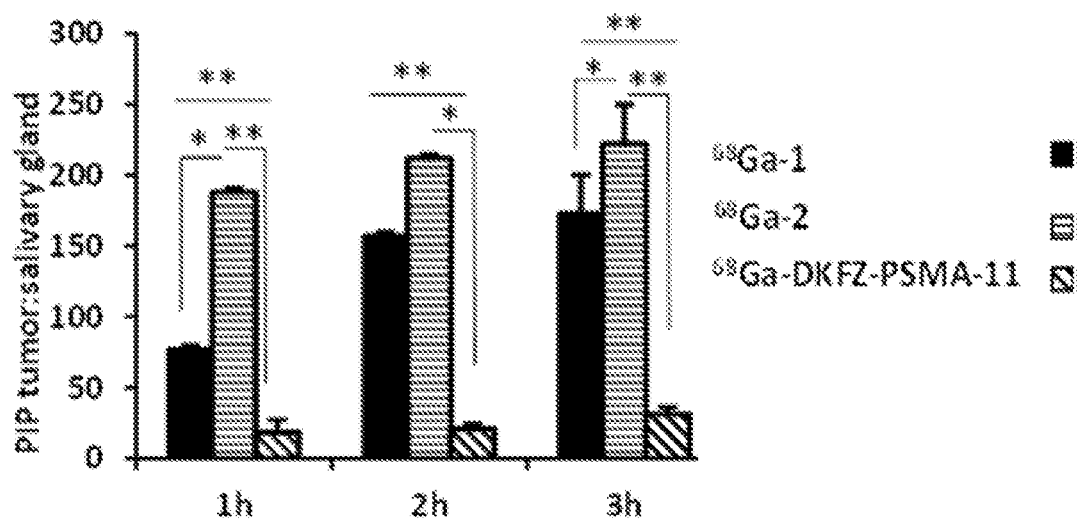
Figure 3D:
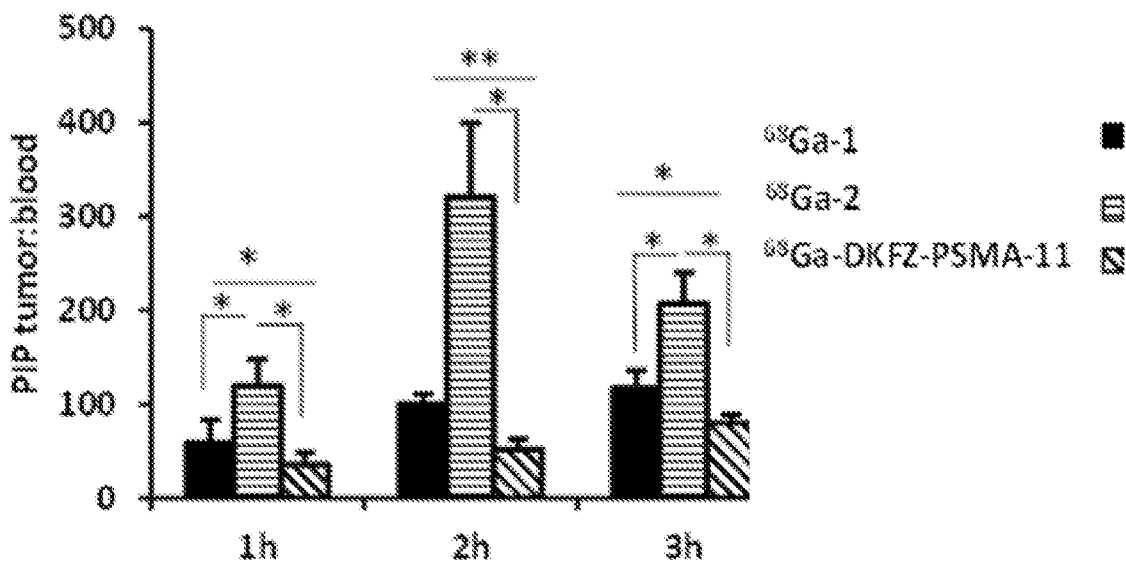

FIG. 2D shows higher spleen uptake for $^{68}$Ga-DKFZ-PSMA-11 compared to either $^{68}$Ga-1 or $^{68}$Ga-2 (P<0.04) at all time-points. Between $^{68}$Ga-1 and $^{68}$Ga-2, the former showed significantly lower spleen (P<0.03) uptake at 1 h and 2 h post-injection compared to the latter. Selected PSMA+ PC3 PIP tumor-to-background for the three agents at 1-3 h post-injection are shown in FIG. 3A, FIG. 3B, FIG. 3C, and FIG. 3D. As anticipated from the biodistribution data, PSMA+ PC3 PIP tumor-to-salivary gland 0.002) and PSMA+ PC3 PIP tumor-to-kidney ratios proved significantly higher for $^{68}$Ga-1 and $^{68}$Ga-2 than for $^{68}$Ga-DKFZ-PSMA-11 (P≤0.04).

PSMA+ PC3 PIP tumor-to-PSMA− PC3 flu tumor ratios were also significantly higher for $^{68}$Ga-1 and $^{68}$Ga-2 compared to $^{68}$Ga-DKFZ-PSMA-11 at 1 h post-injection (P≤0.02). The data show that PSMA+ PC3 PIP tumor-to-blood ratios were highest for $^{68}$Ga-2 at all three time points.

Small Animal PET-CT Imaging.

Whole body PET-CT images were studied for $^{68}$Ga-1, $^{68}$Ga-2 and $^{68}$Ga-DKFZ-PSMA-11 in intact male NOD/SCID mice (FIG. 6) bearing both PSMA+ PC3 PIP and PSMA− PC3 flu xenografts in opposite, upper flanks. Irrespective of charge and lipophilicity, all radiotracers enabled visualization of PSMA+ PC3 PIP tumor and kidneys (FIG. 6). As anticipated from the biodistribution results, for all three agents PSMA+ PC3 PIP tumor was visible as early as 15 min post-injection. Renal uptake of the radiotracers is partially due to the route of excretion of these agents as well as to specific uptake from the expression of PSMA in mouse proximal renal tubules (Silver et al. (1997) *Clin Cancer Res* 3, 81-5.). All three agents showed significant bladder activity, indicating rapid renal clearance. A reduction of the tumor and kidney uptake to background levels was observed with the blocking agent ZJ43 for $^{68}$Ga-2, indicating the receptor-mediated accumulation of the agents.

Example 4

Discussion

Structural optimization of low-molecular-weight imaging and therapeutic agents targeting PSMA is under active investigation (Banerjee et al. (2010) *J Med Chem* 53, 5333-41; Kularatne et al. (2009) *Molecular pharmaceutics* 6, 780-789; Kularatne et al. (2009) *Mol Pharm* 6, 790-800; Nedrow-Byers et al. (2012) *Prostate* 72, 904-12; Nedrow-Byers et al. (2013) *Prostate* 73, 355-62; Nguyen & Tsien (2013) *Nat Rev Cancer* 13, 653-62; Zhang et al. (2010) *J Am Chem Soc* 132, 12711-6; Banerjee et al. (2014) *J Med Chem* 57, 2657-69; Ray Banerjee et al. (2013) *J Med Chem* 56, 6108-21; Anderson et al. (2007) *Bioorg Med Chem* 15, 6678-86; Benesova et al. (2015) *J Nucl Med* 56, 914-20). Such optimization is geared toward high tumor uptake with minimal off-target, namely, renal and salivary gland, uptake at times convenient for imaging and endoradiotherapy. High salivary gland uptake in particular has proved to be a concern. $^{68}$Ga-1 (Banerjee et al. (2010) *J Med Chem* 53, 5333-41) was originally synthesized as its scaffold with the DOTA chelator to enable imaging or therapy, depending on the radionuclide employed. It has been previously showed that a linker to DOTA containing a p-isothiocyanatobenzyl function provided the most suitable pharmacokinetics in a small series of compounds generated for imaging PSMA with $^{86}$Y- and $^{64}$Cu-PET (Banerjee et al. (2014) *J Med Chem* 57, 2657-69; Banerjee et al. (2015) *Journal of nuclear medicine: official publication, Society of Nuclear Medicine* 56, 628-34). NOTA has been shown to be an effective chelating agent for $^{68}$Ga, (stability constant, $K_{ML}$=31.1), compared to for DOTA ($K_{ML}$ -21.3) (Studer & Meares (1992) *Bioconjugate Chemistry* 3, 337-341; Roesch & Riss (2010) *Curr Top Med Chem* 10, 1633-68). The commercially available p-isothiocyanatobenzyl derivative of NOTA has been used in $^{68}$Ga-2 for its mild radiolabeling conditions in the hope of creating a $^{68}$Ga-based agent with improved pharmacokinetics that could be generated simply, as in a kit-like preparation. The in vivo performance characteristics of $^{68}$Ga-1, $^{68}$Ga-2 and $^{68}$Ga-DKFZ-PSMA-11 (Eder et al. (2012) *Bioconjug Chem* 23, 688-97) were compared, the latter of which has been used throughout Europe in clinical trials.

To improve precision with respect to the comparison, all three radiotracers were purified by HPLC to remove unlabeled ligand. The results obtained from biodistribution and imaging experiments indicated that there were no differences in absolute uptake between the three agents in PSMA-expressing tumors (FIG. 2A, FIG. 2B, FIG. 2C, and FIG. 2D, and FIG. 3A, FIG. 3B, FIG. 3C, and FIG. 3D), except for highest uptake for $^{68}$Ga-2 at 1 h post-injection (P<0.007 between $^{68}$Ga-2 and $^{68}$Ga-1). Higher non-target uptake for $^{68}$Ga-DKFZ-PSMA-11 than for $^{68}$Ga-1 or $^{68}$Ga-2 were found, contrary to Eder et al. (Eder et al. (2012) *Bioconjug Chem* 23, 688-97), in which $^{68}$Ga-1 was compared to $^{68}$Ga-DKFZ-PSMA-11 (FIG. 2A, FIG. 2B, FIG. 2C, and FIG. 2D, and FIG. 3A, FIG. 3B, FIG. 3C, and FIG. 3D). Without wishing to be bound to any one particular theory, it is believed that discrepancy derived from the lack of HPLC purification for $^{68}$Ga-1 in Eder et al. (Eder et al. (2012) *Bioconjug Chem* 23, 688-97), which could negatively impact its effective specific activity. Another possibility could be the discrepant tumor models used, with LNCaP used in the earlier report (Eder et al. (2012) *Bioconjug Chem* 23, 688-97), and PSMA+ PC3 PIP for the PSMA-expressing positive control. However, it has been previously reported that the levels of expression of PSMA in PSMA+ PC3 PIP tumors were very similar to that in LNCaP (Banerjee et al. (2011) *Angewandte Chemie* 50, 9167-70.

As previously shown by several groups in the field of PSMA imaging with low-molecular-weight agents (Eder et al. (2012) *Bioconjug Chem* 23, 688-97; Reske et al. (2013) *Mol Imaging* 40, 969-70; Banerjee, et al. (2014) *J Med Chem* 57, 2657-69; Weineisen et al. (2014) *EJNMMI Res.* 4, 1-15; Banerjee et al. (2015) *J Nucl Med* accepted; Banerjee et al. (2011) *Oncotarget* 2, 1244-53; 57; Banerjee et al. *International Symposium on Radiopharmaceutical Sciences*, Amsterdam, The Netherlands, 2011; Vol. 2011, p S65; Nedrow et al. (2015) *Mol Imaging Biol*), the key parameter of non-specific tissue uptake depends on the overall physicochemical properties of the radiolabeled agent, including the metabolic stability of the metal-chelate complex, charge and lipophilicity. Both the chelating agent and the linker employed to attach the radionuclide to the targeting agent are important in establishing those physicochemical features—particularly for compounds <1,500 Da. For example, it has been shown that certain $^{99m}$Tc-oxo cores with different combinations of NxSy-based chelating agents demonstrated high retention in kidney and spleen for more than 6 h (Ray Banerjee et al. (2013) *J Med Chem* 56, 6108-21). Such agents displayed high PSMA+ tumor retention. On the other hand, $^{99m}$Tc(CO)$_3$-based agents showed much faster clearance from most normal tissues including kidneys, although, these agents showed slightly higher gastrointestinal uptake at initial time-points (<2 h) (Banerjee et al. (2013) *J. Med. Chem.* (submitted). High kidney uptake and retention for NOTA-chelated $^{64}$Cu-labeled PSMA-inhibitor were observed, compared to the CB-TE2A-conjugated $^{64}$Cu-labeled agent (Banerjee et al. (2014) *J Med Chem* 57, 2657-69) although both chelating agents are known to form a copper complex with comparable stability (Dumont et al. (2011) *Journal of nuclear medicine: official publication, Society of Nuclear Medicine* 52, 1276-84; Fani et al. (2011) *Journal of nuclear medicine: official publication, Society of Nuclear Medicine* 52, 1110-8). Modifying linker and chelating agent indeed revealed significant changes in biodistribution pattern as reported by Eder et al. (Benesova et al. (2015) *J Nucl Med* 56, 914-20). A direct comparison of DOTA-mono amide chelated PSMA-targeting agent, $^{68}$Ga-DKFZ-PSMA-617 vs HBED-CC-conjugated $^{68}$Ga-DKFZ-PSMA-11 in preclinical studies demonstrated higher tumor uptake at later time points, lower spleen accumulation, and fast activity clearance from the kidneys.

In summary, a preclinical comparative study to evaluate the in vivo pharmacokinetics of three $^{68}$Ga-labeled PSMA-targeting PET radiopharmaceuticals has been reported. The macrocyclic NOTA chelated agent $^{68}$Ga-2 demonstrated the highest PSMA+ tumor accumulation at clinically convenient times post-injection, and showed rapid clearance from most normal tissues, including kidney and salivary gland. $^{68}$Ga-2 is a clinically viable imaging agent for detecting PSMA+ lesions.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

International PCT Patent Application Publication No. PCT/US2008/007947 to Pomper, M. G.; Ray, S.; Mease, R. C.; Foss, C. for Labeled inhibitors of prostate specific membrane antigen (PSMA), biological evaluation, and use as imaging agents, published Dec. 31, 2008 (WO 2009/002529 A2).

International PCT Patent Application Publication No. PCT/US2010/028020 to Pomper, M. G.; Mease, R. C.; Ray, S.; Chen, Y. for PSMA-targeting compounds and uses thereof, published Sep. 23, 2010 (WO 2010/108125 A2).

International PCT Patent Application Publication No. PCT/US2011/026238 to Low, P. S.; Chelvam, V.; Kim, Y. for PSMA binding linker conjugates and methods for using, published Sep. 1, 2011 (WO 2011/106639; WO 2010/045598 A2; WO 2009/026177A1).

United States Patent Application Publication No. US 2013/0034494 A1 to Babich, J. W.; Zimmerman, C.; Joyal, J. L.; Lu, G. for Radiolabeled Prostate Specific Membrane Antigen Inhibitors, published Feb. 7, 2013.

Afshar-Oromieh, A.; Avtzi, E.; Giesel, F. L.; Holland-Letz, T.; Linhart, H. G.; Eder, M.; Eisenhut, M.; Boxler, S.; Hadaschik, B. A.; Kratochwil, C.; Weichert, W.; Kopka, K.; Debus, J.; Haberkorn, U. The diagnostic value of PET/CT imaging with the Ga-labelled PSMA ligand HBED-CC in the diagnosis of recurrent prostate cancer. *Eur J Nucl Med Mol Imaging* 2014.

Afshar-Oromieh, A.; Avtzi, E.; Giesel, F. L.; Holland-Letz, T.; Linhart, H. G.; Eder, M.; Eisenhut, M.; Boxler, S.; Hadaschik, B. A.; Kratochwil, C.; Weichert, W.; Kopka, K.; Debus, J.; Haberkorn, U. The diagnostic value of PET/CT imaging with the (68)Ga-labelled PSMA ligand HBED-CC in the diagnosis of recurrent prostate cancer. *Eur. J. Nuc.l Med. Mol. Imaging* 2015, 42, 197-209.

Afshar-Oromieh, A.; Haberkorn, U.; Schlemmer, H. P.; Fenchel, M.; Eder, M.; Eisenhut, M.; Hadaschik, B. A.; Kopp-Schneider, A.; Rothke, M. Comparison of PET/CT and PET/MRI hybrid systems using a $^{68}$Ga-labelled PSMA ligand for the diagnosis of recurrent prostate cancer: initial experience. *Eur J Nucl Med Mol Imaging* 2014, 41, 887-97.

Afshar-Oromieh, A.; Haberkorn, U.; Eder, M.; Eisenhut, M.; Zechmann, C. M. [68Ga]Gallium-labelled PSMA ligand as superior PET tracer for the diagnosis of prostate cancer: comparison with 18F-FECH. *Eur J Nucl Med Mol Imaging* 2012, 39, 1085-6.

Afshar-Oromieh, A.; Haberkorn, U.; Hadaschik, B.; Habl, G.; Eder, M.; Eisenhut, M.; Schlemmer, H. P.; Roethke, M. C. PET/MRI with a $^{68}$Ga-PSMA ligand for the detection of prostate cancer. *Eur J Nucl Med Mol Imaging* 2013, 40, 1629-30.

Afshar-Oromieh, A.; Malcher, A.; Eder, M.; Eisenhut, M.; Linhart, H. G.; Hadaschik, B. A.; Holland-Letz, T.; Giesel, F. L.; Kratochwil, C.; Haufe, S.; Haberkorn, U.; Zechmann, C. M. PET imaging with a [68Ga]gallium-labelled PSMA ligand for the diagnosis of prostate cancer: biodistribution in humans and first evaluation of tumour lesions. *Eur J Nucl Med Mol Imaging* 2013, 40, 486-95.

Afshar-Oromieh, A.; Malcher, A.; Eder, M.; Eisenhut, M.; Linhart, H. G.; Hadaschik, B. A.; Holland-Letz, T.; Giesel, F. L.; Kratochwil, C.; Haufe, S.; Haberkorn, U.; Zechmann, C. M. Reply to Reske et al.: PET imaging with a [68Ga]gallium-labelled PSMA ligand for the diagnosis of prostate cancer: biodistribution in humans and first evaluation of tumour lesions. *Eur J Nucl Med Mol Imaging* 2013, 40, 971-2.

Anderson, M. O.; Wu, L. Y.; Santiago, N. M.; Moser, J. M.; Rowley, J. A.; Bolstad, E. S.; Berkman, C. E. Substrate specificity of prostate-specific membrane antigen. *Bioorg Med Chem* 2007, 15, 6678-86.

Baccala, A.; Sercia, L.; Li, J.; Heston, W.; Zhou, M. Expression of prostate-specific membrane antigen in tumor-associated neovasculature of renal neoplasms. *Urology* 2007, 70, 385-90.

Banerjee, S. R. P., M.; Byun, Y.; Nimmagadda, S.; Baidoo, K. E.; Brechbiel, M.; Mease, R. C.; Pomper, M. G. Preclinical evaluation of 86Y-Labeled inhibitors of prostate specific membrane antigen In 19*th International Symposium on Radiopharmaceutical Sciences*, Amsterdam, The Netherlands, 2011; Vol. 2011, p S65.

Banerjee S R, Foss C A, et al. Synthesis and evaluation of technetium-99m- and rhenium-labeled inhibitors of the prostate-specific membrane Antigen(PSMA). *J. Med. Chem.* 51: 4504-4517 (2008).

Banerjee, S. R.; Foss, C. A.; Pullambhatla, M.; Wang, Y.; Srinivasan, S.; Hobbs, R. F.; Baidoo, K. E.; Brechbiel, M. W.; Nimmagadda, S.; Mease, R. C.; Sgouros, G.; Pomper, M. G. Preclinical evaluation of 86Y-labeled inhibitors of prostate-specific membrane antigen for dosimetry estimates. *Journal of nuclear medicine: official publication, Society of Nuclear Medicine* 2015, 56, 628-34.

Banerjee, S. R.; Pullambhatla, M.; Byun, Y.; Nimmagadda, S.; Green, G.; Fox, J. J.; Horti, A.; Mease, R. C.; Pomper, M. G. $^{68}$Ga-labeled inhibitors of prostate-specific membrane antigen (PSMA) for imaging prostate cancer. *J Med Chem* 2010, 53, 5333-41.

Banerjee, S. R.; Pullambhatla, M.; Byun, Y.; Nimmagadda, S.; Foss, C. A.; Green, G.; Fox, J. J.; Lupold, S. E.; Mease, R. C.; Pomper, M. G. Sequential SPECT and Optical Imaging of Experimental Models of Prostate Cancer with a Dual Modality Inhibitor of the Prostate-Specific Membrane Antigen. *Angewandte Chemie* 2011, 50, 9167-70.

Banerjee, S. R.; Pullambhatla, M.; Foss, C. A.; Nimmagadda, S.; Ferdani, R.; Anderson, C. J.; Mease, R. C.; Pomper, M. G. (6)(4)Cu-labeled inhibitors of prostate-specific membrane antigen for PET imaging of prostate cancer. *J Med Chem* 2014, 57, 2657-69.

Banerjee, S. R.; Pullambhatla, M.; Foss, C. A.; Falk, A.; Byun, Y.; Nimmagadda, S.; Mease, R. C.; Pomper, M. G. Effect of chelators on the pharmacokinetics of (99m)Tc-labeled imaging agents for the prostate-specific membrane antigen (PSMA). *J Med Chem* 2013, 56, 6108-21.

Banerjee, S. R.; Pullambhatla, M.; Shallal, H.; Lisok, A.; Mease, R. C.; Pomper, M. G. A modular strategy to prepare multivalent inhibitors of prostate-specific membrane antigen (PSMA). *Oncotarget* 2011, 2, 1244-53.

Baur, B.; Solbach, C.; Andreolli, E.; Winter, G.; Machulla, H. J.; Reske, S. N. Synthesis, Radiolabelling and In Vitro Characterization of the Gallium-68-, Yttrium-90- and Lutetium-177-Labelled PSMA Ligand, CHX-A"-DTPA-DUPA-Pep. *Pharmaceuticals (Basel)* 2014, 7, 517-29.

Benesova, M.; Schafer, M.; Bauder-Wust, U.; Afshar-Oromieh, A.; Kratochwil, C.; Mier, W.; Haberkorn, U.; Kopka, K.; Eder, M. Preclinical Evaluation of a Tailor-Made DOTA-Conjugated PSMA Inhibitor with Optimized Linker Moiety for Imaging and Endoradiotherapy of Prostate Cancer. *J Nucl Med* 2015, 56, 914-20.

Broan, C. J.; COX, J. P. L.; Craig, A. S.; Kataky, R.; Parker, D.; Harrison, A.; Randall, A. M.; Ferguson, G. Structure and Solution Stability of Indium and Gallium Complexes of 1,4,7-Triazacyclononanetriacetate and of Yttrium Complexes of 1,4,7,1 O-Tetraazacyclododecanetetraacetate and Related Ligands: Kinetically Stable Complexes for Use in Imaging and Radioimmunotherapy. X-Ray Molecular Structure of the Indium and Gallium Complexes of 1,4,7-Triazacyclononane-I,4,7-triacetic Acid *J. CHEM. SOC. PERKIN TRANS.* 1991, 2, 87-99.

Chang, S. S.; Gaudin, P. B.; Reuter, V. E.; O'Keefe, D. S.; Bacich, D. J.; Heston, W. D. Prostate-Specific Membrane Antigen: Much More Than a Prostate Cancer Marker. *Mol Urol* 1999, 3, 313-320.

Chang, S. S.; O'Keefe, D. S.; Bacich, D. J.; Reuter, V. E.; Heston, W. D.; Gaudin, P. B. Prostate-specific membrane antigen is produced in tumor-associated neovasculature. *Clin Cancer Res* 1999, 5, 2674-81.

Cheng, Y.; Prusoff, W. H. Relationship between the inhibition constant (K1) and the concentration of inhibitor which causes 50 percent inhibition (I50) of an enzymatic reaction. *Biochemical pharmacology* 1973, 22, 3099-108.

Cho, S. Y.; Gage, K. L.; Mease, R. C.; Senthamizhchelvan, S.; Holt, D. P.; Jeffrey-Kwanisai, A.; Endres, C. J.; Dannals, R. F.; Sgouros, G.; Lodge, M.; Eisenberger, M. A.; Rodriguez, R.; Carducci, M. A.; Rojas, C.; Slusher, B. S.; Kozikowski, A. P.; Pomper, M. G. Biodistribution, tumor detection, and radiation dosimetry of 18F-DCFBC, a low-molecular-weight inhibitor of prostate-specific membrane antigen, in patients with metastatic prostate cancer. *J Nucl Med* 2012, 53, 1883-91.

Dumont, R. A.; Deininger, F.; Haubner, R.; Maecke, H. R.; Weber, W. A.; Fani, M. Novel (64)Cu- and (68)Ga-labeled RGD conjugates show improved PET imaging of alpha (nu)beta(3) integrin expression and facile radiosynthesis. *Journal of nuclear medicine: official publication, Society of Nuclear Medicine* 2011, 52, 1276-84.

Eder, M.; Schafer, M.; Bauder-Wust, U.; Hull, W. E.; Wangler, C.; Mier, W.; Haberkorn, U.; Eisenhut, M. $^{68}$Ga-complex lipophilicity and the targeting property of a urea-based PSMA inhibitor for PET imaging. *Bioconjug Chem* 2012, 23, 688-97.

Eder, M.; Wangler, B.; Knackmuss, S.; LeGall, F.; Little, M.; Haberkorn, U.; Mier, W.; Eisenhut, M. Tetrafluorophenolate of HBED-CC: a versatile conjugation agent for 68Ga-labeled small recombinant antibodies. *European Journal of Nuclear Medicine and Molecular Imaging* 2008, 35, 1878-1886.

Eiber, M.; Maurer, T.; Kubler, H.; Gschwend, J. E.; Souvatzoglou, M.; Ruffani, A.; Graner, F.-P.; Schwaiger, M.; Beer, A. J.; Haller, B.; Haberhorn, U.; Eisenhut, M.; Wester, H.-J. Evaluation of Hybrid 68Ga-PSMA Ligand PET/CT in 248 Patients with Biochemical Recurrence After Radical Prostatectomy. *J Nucl Med* 2015, 56, 668-74.

Eiber, M.; Nekolla, S. G.; Maurer, T.; Weirich, G.; Wester, H.-J.; Schwaiger, M. (68)Ga-PSMA PET/MR with multimodality image analysis for primary prostate cancer. *Abdom Imaging* 2014.

Fani, M.; Andre, J. P.; Maecke, H. R. 68Ga-PET: a powerful generator-based alternative to cyclotron-based PET radiopharmaceuticals. *Contrast media & molecular imaging* 2008, 3, 67-77.

Fani, M.; Del Pozzo, L.; Abiraj, K.; Mansi, R.; Tamma, M. L.; Cescato, R.; Waser, B.; Weber, W. A.; Reubi, J. C.; Maecke, H. R. PET of somatostatin receptor-positive tumors using 64Cu- and $^{68}$Ga-somatostatin antagonists: the chelate makes the difference. *Journal of nuclear medicine: official publication, Society of Nuclear Medicine* 2011, 52, 1110-8.

Haffner, M. C.; Kronberger, I. E.; Ross, J. S.; Sheehan, C. E.; Zitt, M.; Muhlmann, G.; Ofner, D.; Zelger, B.; Ensinger, C.; Yang, X. J.; Geley, S.; Margreiter, R.; Bander, N. H. Prostate-specific membrane antigen expression in the neovasculature of gastric and colorectal cancers. *Hum Pathol* 2009, 40, 1754-61.

Haffner, M. C.; Laimer, J.; Chaux, A.; Schafer, G.; Obrist, P.; Brunner, A.; Kronberger, I. E.; Laimer, K.; Gurel, B.; Koller, J. B.; Seifarth, C.; Zelger, B.; Klocker, H.; Rasse, M.; Doppler, W.; Bander, N. H. High expression of prostate-specific membrane antigen in the tumor-associated neo-vasculature is associated with worse prognosis in squamous cell carcinoma of the oral cavity. *Mod Pathol* 2012, 25, 1079-85.

Herrmann, K.; Bluemel, C.; Weineisen, M.; Schottelius, M.; Wester, H.-J.; Czernin, J.; Eberlein, U.; Beykan, S.; Lapa, C.; Riedmiller, H.; Krebs, M.; Kropf, S.; Schirbel, A.; Buck, A. K.; Lassmann, M. Biodistribution and radiation dosimetry for a novel probe targeting prostate specific membrane antigen for Imaging and Therapy (68Ga-PSMA I&T). *Journal of Nuclear Medicine* 2015.

Institute, N. C. Cancer Statistics http://seer.cancer.gov/statfacts/html/prost.html 2015.

Kularatne, S. A.; Wang, K.; Santhapuram, H.-K. R.; Low, P. S. Prostate-specific membrane antigen targeted imaging and therapy of prostate cancer using a PSMA inhibitor as a homing ligand. *Molecular pharmaceutics* 2009, 6, 780-789.

Kularatne, S. A.; Zhou, Z.; Yang, J.; Post, C. B.; Low, P. S. Design, synthesis, and preclinical evaluation of prostate-specific membrane antigen targeted (99m)Tc-radioimaging agents. *Mol Pharm* 2009, 6, 790-800.

L'Eplattenier, F. L.; Murase, I.; Martel, A. E. New Multidentate Ligands. VI. Chelating Tendencies of N,N-Di (2-hydroxybenzyl) ethylenediamine-N,N-diacetic Acid. *Journal of the American Chemical Society* 1967, 89.

Mottaghy, F.; Behrendt, F.; Verburg, F. 68Ga-PSMA-HBED-CC PET/CT: where molecular imaging has an edge over morphological imaging. *European Journal of Nuclear Medicine and Molecular Imaging* 2015, 1-3.

Murphy, G. P.; Greene, T. G.; Tino, W. T.; Boynton, A. L.; Holmes, E. H. Isolation and characterization of monoclonal antibodies specific for the extracellular domain of prostate specific membrane antigen. *J Urol* 1998, 160, 2396-401.

Murphy, G. P.; Holmes, E. H.; Boynton, A. L.; Kenny, G. M.; Ostenson, R. C.; Erickson, S. J.; Barren, R. J. Comparison of prostate specific antigen, prostate specific membrane antigen, and LNCaP-based enzyme-linked immunosorbent assays in prostatic cancer patients and patients with benign prostatic enlargement. *Prostate* 1995, 26, 164-8.

Murphy, G. P.; Kenny, G. M.; Ragde, H.; Wolfert, R. L.; Boynton, A. L.; Holmes, E. H.; Misrock, S. L.; Bartsch, G.; Klocker, H.; Pointner, J.; Reissigl, A.; McLeod, D. G.; Douglas, T.; Morgan, T.; Gilbaugh, J., Jr. Measurement of serum prostate-specific membrane antigen, a new prognostic marker for prostate cancer. *Urology* 1998, 51, 89-97.

Nedrow, J. R.; Latoche, J. D.; Day, K. E.; Modi, J.; Ganguly, T.; Zeng, D.; Kurland, B. F.; Berkman, C. E.; Anderson, C. J. Targeting PSMA with a Cu-64 Labeled Phosphoramidate Inhibitor for PET/CT Imaging of Variant PSMA-Expressing Xenografts in Mouse Models of Prostate Cancer. *Mol Imaging Biol* 2015.

Nedrow-Byers, J. R.; Jabbes, M.; Jewett, C.; Ganguly, T.; He, H.; Liu, T.; Benny, P.; Bryan, J. N.; Berkman, C. E. A phosphoramidate-based prostate-specific membrane antigen-targeted SPECT agent. *Prostate* 2012, 72, 904-12.

Nedrow-Byers, J. R.; Moore, A. L.; Ganguly, T.; Hopkins, M. R.; Fulton, M. D.; Benny, P. D.; Berkman, C. E. PSMA-targeted SPECT agents: mode of binding effect on in vitro performance. *Prostate* 2013, 73, 355-62.

Nguyen, Q. T.; Tsien, R. Y. Fluorescence-guided surgery with live molecular navigation—a new cutting edge. *Nat Rev Cancer* 2013, 13, 653-62.

Olszewski, R. T.; Bukhari, N.; Zhou, J.; Kozikowski, A. P.; Wroblewski, J. T.; Shamimi-Noori, S.; Wroblewska, B.; Bzdega, T.; Vicini, S.; Barton, F. B.; Neale, J. H. NAAG peptidase inhibition reduces locomotor activity and some stereotypes in the PCP model of schizophrenia via group II mGluR. *Journal of neurochemistry* 2004, 89, 876-85.

Reske, S. N.; Winter, G.; Baur, B.; Machulla, H. J.; Kull, T. Comment on Afshar-Oromieh et al.: PET imaging with a [68Ga]gallium-labelled PSMA ligand for the diagnosis of prostate cancer: biodistribution in humans and first evaluation of tumour lesions. *Eur J Nucl Med Mol Imaging* 2013, 40, 969-70.

Roesch, F.; Riss, P. J. The renaissance of the (6)(8)Ge/(6)(8)Ga radionuclide generator initiates new developments in (6)(8)Ga radiopharmaceutical chemistry. *Curr Top Med Chem* 2010, 10, 1633-68.

Rowe, S. P.; Gage, K. L.; Faraj, S. F.; Macura, K. J.; Cornish, T. C.; Gonzalez-Roibon, N.; Guner, G.; Munari, E.; Partin, A. W.; Pavlovich, C. P.; Han, M.; Carter, H. B.; Bivalacqua, T. J.; Blackford, A.; Holt, D.; Dannals, R. F.; Netto, G. J.; Lodge, M. A.; Mease, R. C.; Pomper, M. G.; Cho, S. Y. 18F-DCFBC PET/CT for PSMA-Based Detection and Characterization of Primary Prostate Cancer. *J Nucl Med* 2015, 56, 1003-10.

Silver, D. A.; Pellicer, I.; Fair, W. R.; Heston, W. D.; Cordon-Cardo, C. Prostate-specific membrane antigen expression in normal and malignant human tissues. *Clin Cancer Res* 1997, 3, 81-5.

Studer, M.; Meares, C. F. Synthesis of novel 1,4,7-triazacyclononane-N,N',N"-triacetic acid derivatives suitable for protein labeling. *Bioconjugate Chemistry* 1992, 3, 337-341.

Sweat, S. D.; Pacelli, A.; Murphy, G. P.; Bostwick, D. G. Prostate-specific membrane antigen expression is greatest in prostate adenocarcinoma and lymph node metastases. *Urology* 1998, 52, 637-40.

Wang H-l, W. S.-s., Song W-h, Pan Y, Yu H-p, Si T-g, et al. Expression of Prostate-Specific Membrane Antigen in Lung Cancer Cells and Tumor Neovasculature Endothelial Cells and Its Clinical Significance. *PLoS ONE* 2015, 10.

Weineisen, M.; Simecek, J.; Schottelius, M.; Schwaiger, M.; Wester, H.-J. Synthesis and preclinical evaluation of DOTAGA-conjugated PSMA ligands for functional imaging and endoradiotherapy of prostate cancer. *EJNMMI Res.* 2014, 4, 1-15;

Weineisen, M.; Simecek, J.; Schottelius, M.; Schwaiger, M.; Wester, H. J. Synthesis and preclinical evaluation of DOTAGA-conjugated PSMA ligands for functional imaging and endoradiotherapy of prostate cancer. *EJNMMI Res* 2014, 4, 63.

Weineisen, M.; Schottelius, M.; Simecek, J.; Baum, R. P.; Yildiz, A.; Beykan, S.; Kulkarni, H. R.; Lassmann, M.; Klette, I.; Eiber, M.; Schwaiger, M.; Wester, H. J. 68Ga- and 177Lu-labeled PSMA I&T: Optimization of a PSMA targeted theranostic concept and first proof of concept human studies. *J Nucl Med* 2015.

Zhang, A. X.; Murelli, R. P.; Barinka, C.; Michel, J.; Cocleaza, A.; Jorgensen, W. L.; Lubkowski, J.; Spiegel, D. A. A remote arene-binding site on prostate specific membrane antigen revealed by antibody-recruiting small molecules. *J Am Chem Soc* 2010, 132, 12711-6.

Zhernosekov, K. P.; Filosofov, D. V.; Baum, R. P.; Aschoff, P.; Bihl, H.; Razbash, A. A.; Jahn, M.; Jennewein, M.; Rosch, F. Processing of generator-produced 68Ga for medical application. *J Nucl Med* 2007, 48, 1741-8.

Zoller, M.; Schuhmacher, J.; Reed, J.; Maier-Borst, W.; Matzku, S. Establishment and Characterization of Monoclonal Antibodies Against an Octahedral Gallium Chelate Suitable for Immunoscintigraphy with PET. *Journal of Nuclear Medicine* 1992, 33, 1366-1372.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound having the following chemical structure:

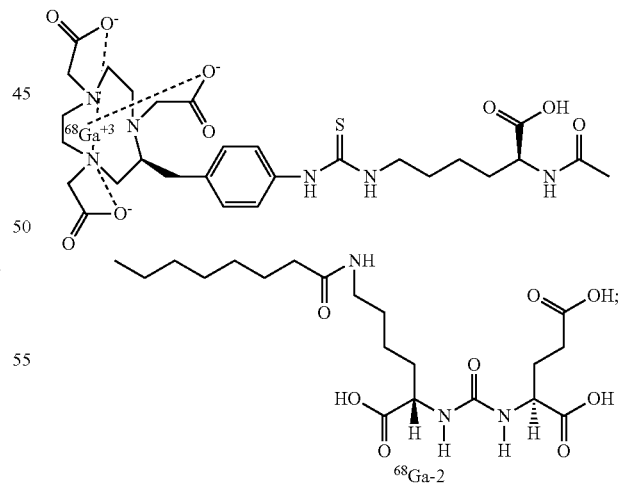

and pharmaceutically acceptable salts thereof.

2. A method for imaging one or more prostate-specific membrane antigen (PSMA) tumors, or cells the method comprising contacting the one or more tumors, or cells, with an effective amount of a compound having the following chemical structure and making an image:

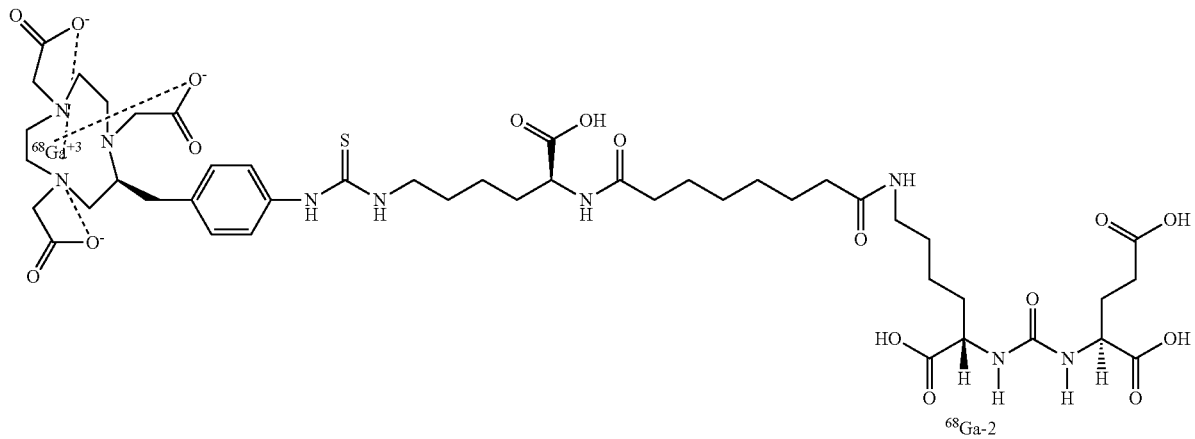

68Ga-2 and pharmaceutically acceptable salts thereof.

3. The method of claim 2, wherein the imaging comprises positron emission tomography (PET).

4. The method of claim 2, wherein the imaging comprises single-photon emission computed tomography (SPECT).

5. The method of claim 2, wherein the one or more PSMA-expressing tumors or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof.

6. The method of claim 2, wherein the one or more PSMA-expressing tumors or cells is a prostate tumor or cell.

7. The method of claim 2, wherein the one or more PSMA-expressing tumors or cells is in vitro, in vivo or ex-vivo.

8. The method of claim 2, wherein the one or more PSMA-expressing tumors or cells is present in a subject.

9. The method of claim 8, wherein the compound comprising the radioactive metal suitable for imaging is cleared from the tumor or cell in the subject.

10. The method of claim 8, wherein the compound comprising the radioactive metal suitable for imaging is cleared more rapidly from a subject's kidneys than from a tumor of the subject.

11. The method of claim 2, wherein the compound comprising the radioactive metal suitable for imaging substantially localizes to the tumor or cell within about 60 minutes of administration.

12. A kit comprising a compound according to claim 1.

* * * * *